(12) United States Patent
Svedman

(10) Patent No.: US 6,254,580 B1
(45) Date of Patent: Jul. 3, 2001

(54) SUCTION BLISTER SAMPLING

(76) Inventor: Pal Svedman, Chemin de Sous-Balme 9, CH-1255, Veyrier (CH)

( * ) Notice: Subject to any disclaimer, the term of this patent is extended or adjusted under 35 U.S.C. 154(b) by 0 days.

(21) Appl. No.: 08/945,642

(22) PCT Filed: Apr. 24, 1996

(86) PCT No.: PCT/EP96/01708

§ 371 Date: Jun. 9, 1998

§ 102(e) Date: Jun. 9, 1998

(87) PCT Pub. No.: WO96/33768

PCT Pub. Date: Oct. 31, 1996

(30) Foreign Application Priority Data

Apr. 27, 1995 (GB) .................................................. 9508606

(51) Int. Cl.[7] .................................................. A61M 1/00
(52) U.S. Cl. .......................................... 604/313; 604/115
(58) Field of Search .................................. 604/181, 115, 604/200, 201, 212, 313–316

(56) References Cited

U.S. PATENT DOCUMENTS

| 1,725,488 | * | 8/1929 | Stephani . |
|---|---|---|---|
| 1,934,046 | * | 11/1933 | Demarchi . |
| 2,743,723 | | 5/1956 | Hein . |
| 3,263,683 | | 8/1966 | Uddenberg . |
| 4,073,288 | | 2/1978 | Chapman . |
| 4,299,219 | * | 11/1981 | Norris, Jr. . |
| 4,781,701 | | 11/1988 | Geprägs . |
| 4,833,384 | | 5/1989 | Munro et al. . |
| 6,048,337 | * | 4/2000 | Svedman . |

FOREIGN PATENT DOCUMENTS

| 1 557 037 | 3/1970 | (DE) . |
|---|---|---|
| 0 248 979 | 12/1987 | (EP) . |
| 0 388 831 | 9/1990 | (EP) . |
| 1 279 632 | 4/1962 | (FR) . |
| 2 589 727 | 5/1987 | (FR) . |
| 1 441 387 | 6/1976 | (GB) . |
| 2 173 910 | 10/1986 | (GB) . |
| 92/11879 | 7/1992 | (WO) . |
| 95/15783 | 6/1995 | (WO) . |

* cited by examiner

Primary Examiner—Anhtuan T. Nguyen
Assistant Examiner—Jeremy Thissell
(74) Attorney, Agent, or Firm—Flehr Hohbach Test Albritton & Herbert LLP

(57) ABSTRACT

There is disclosed an apparatus (1) for use in a suction blister technique of sampling fluid from the human or animal body. The apparatus (1) comprises a cup (2) defining a chamber and having a rim portion (3) defining an aperture (5) communicating with the chamber. An annular flange (6) extends outwardly from the rim portion (3) whereby in use the flange (6) is sealingly attached to the body such that an area of skin closes the aperture (5). A ducted portion (11) is connected to the cup (2) and defines duct (12) which communicates with the chamber. The cup (2) further comprises a roof (4) which merges with the rim portion (3) and is formed of a resiliently deformable material having a shape memory which urges the roof (4) into an expanded configuration in which the roof (4) is held clear of the aperture (5). The roof is however deformable to a collapsed configuration in which it is proximal to the aperture (5).

16 Claims, 21 Drawing Sheets

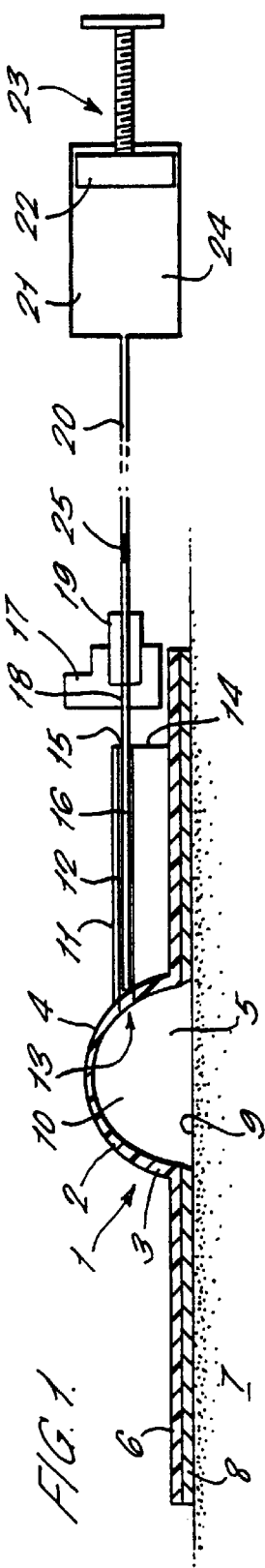
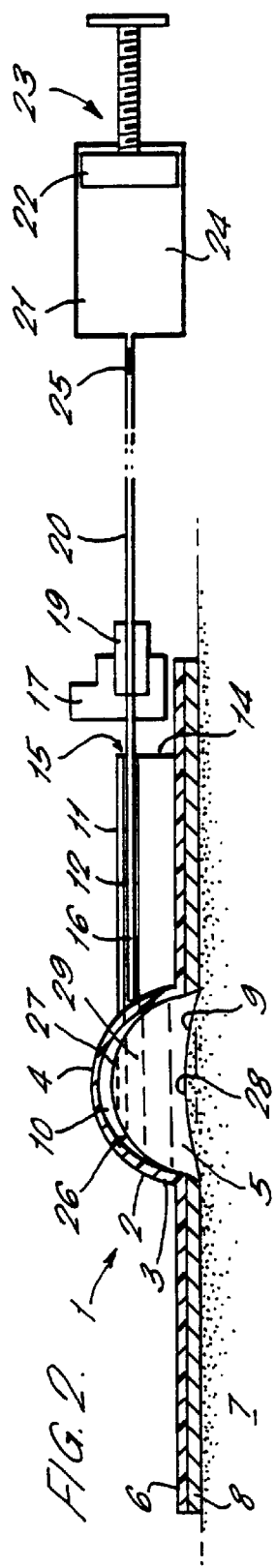
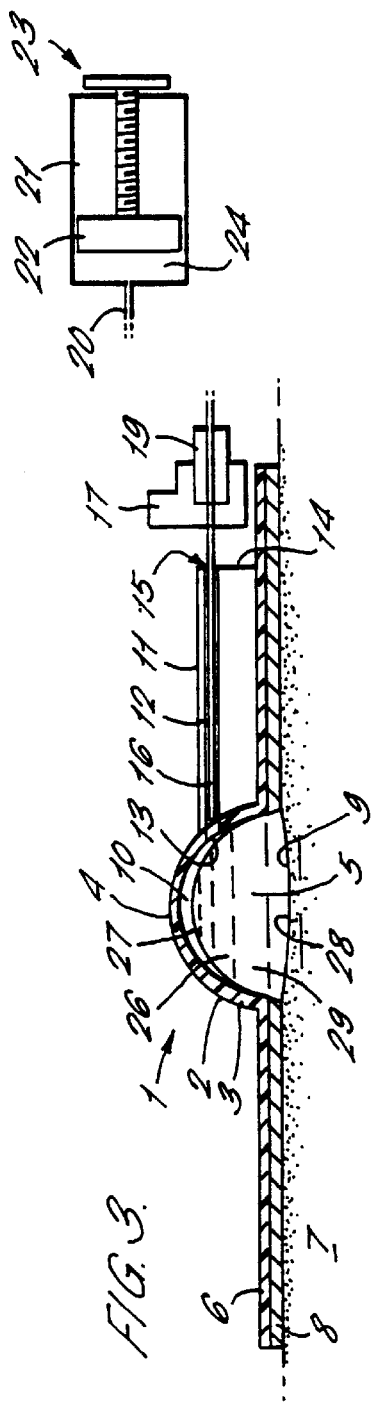

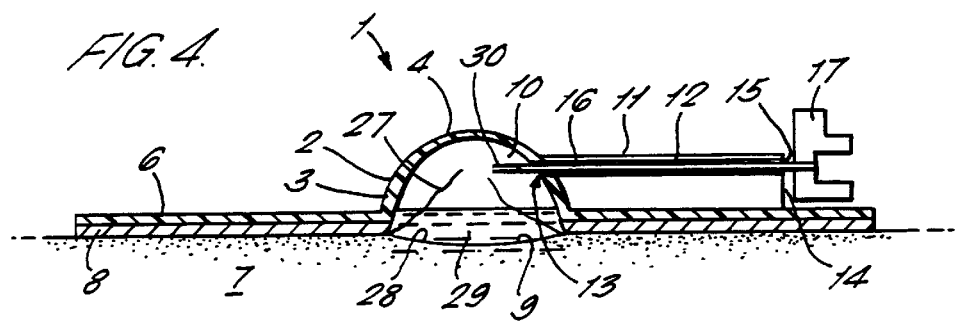
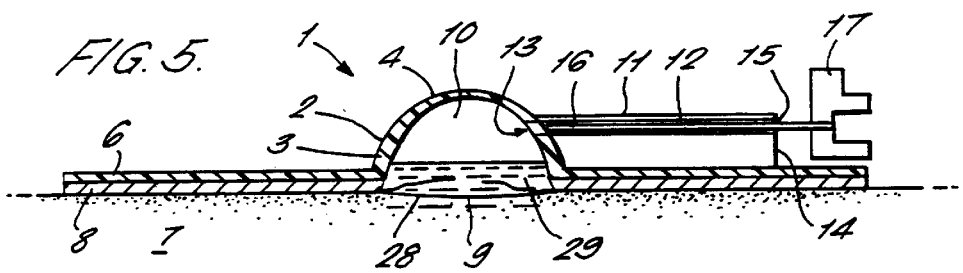
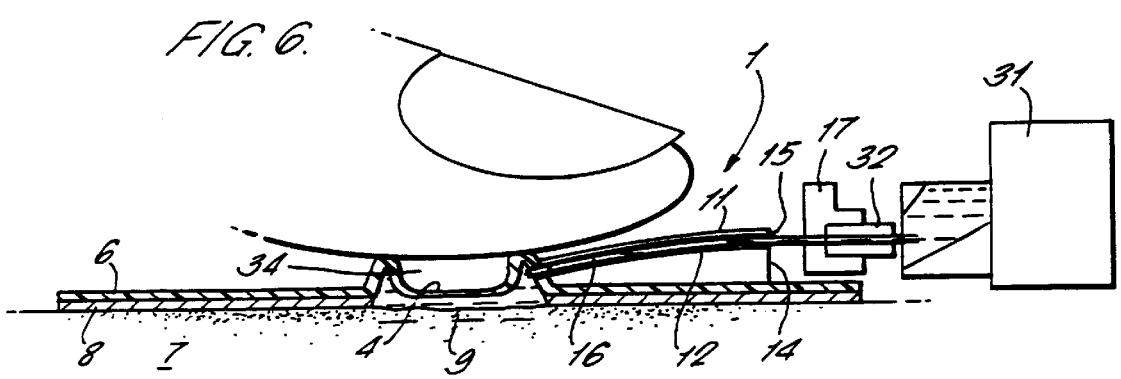
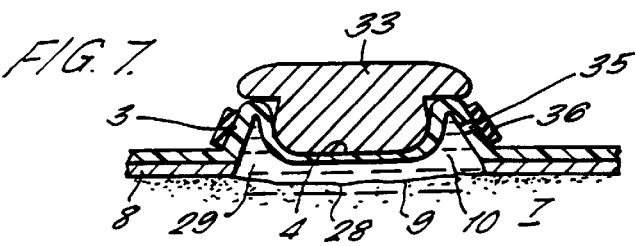

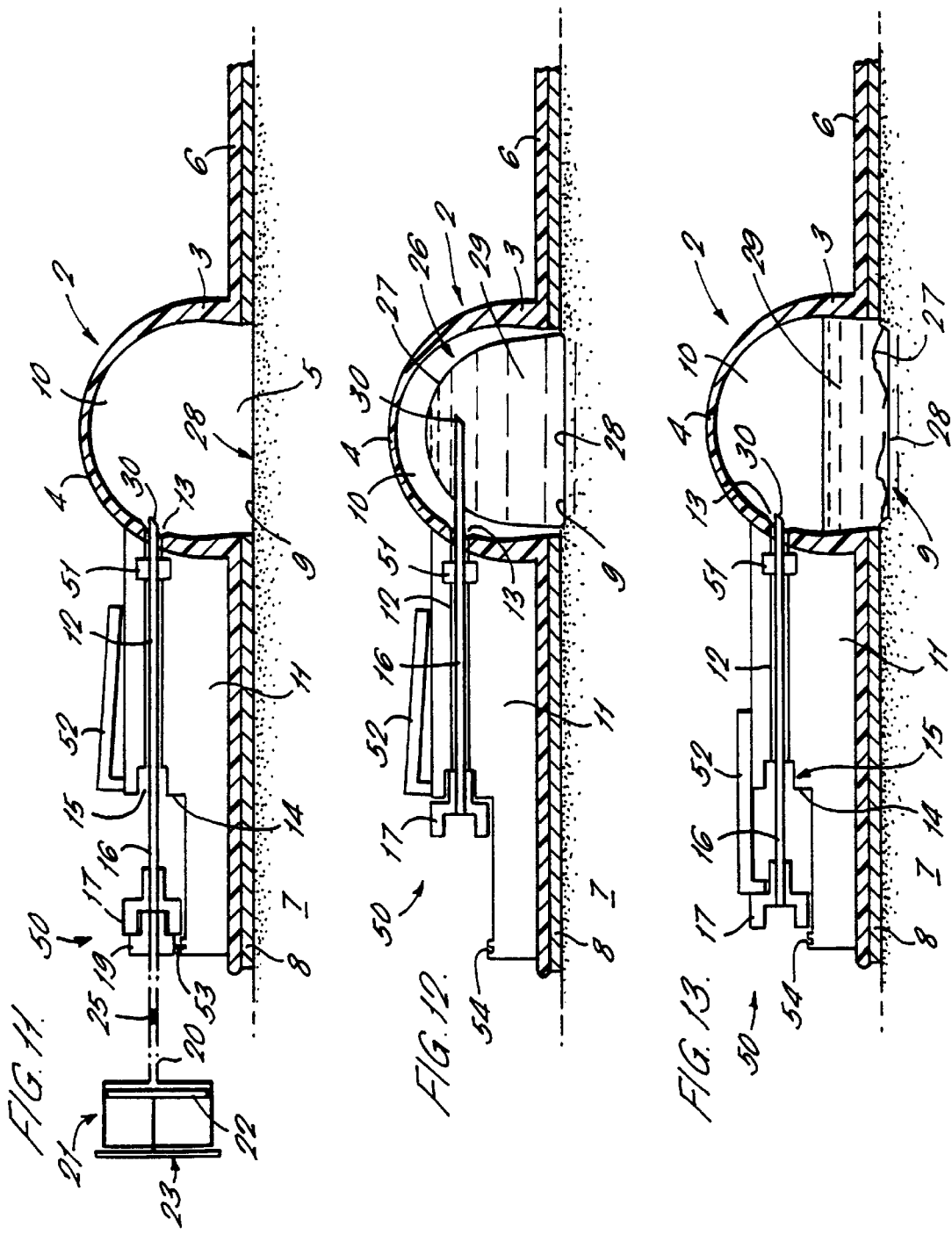

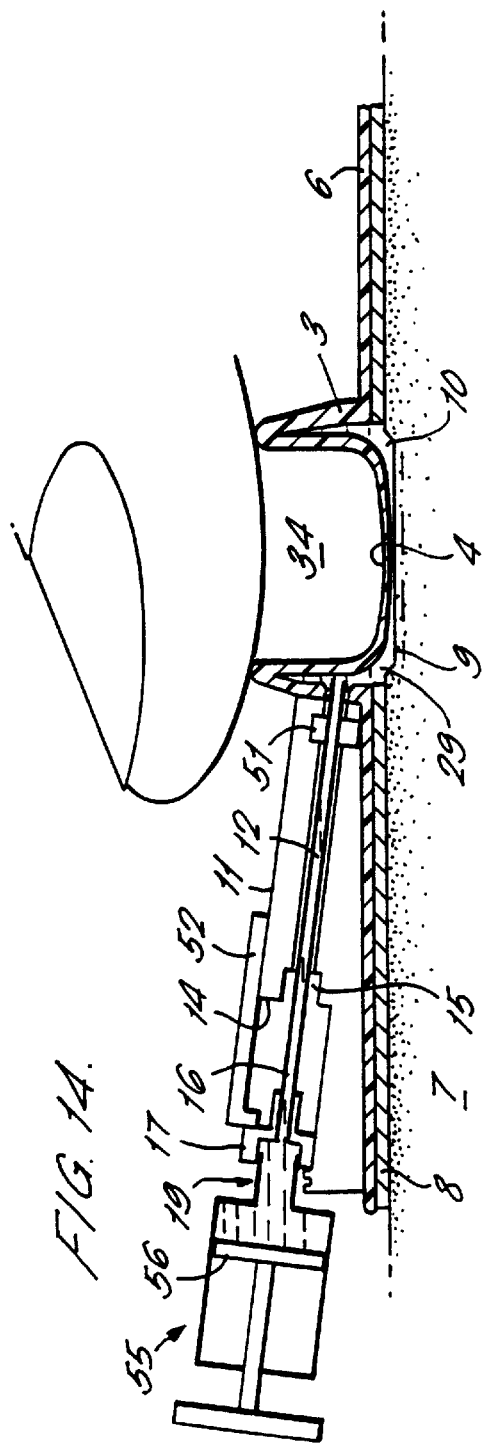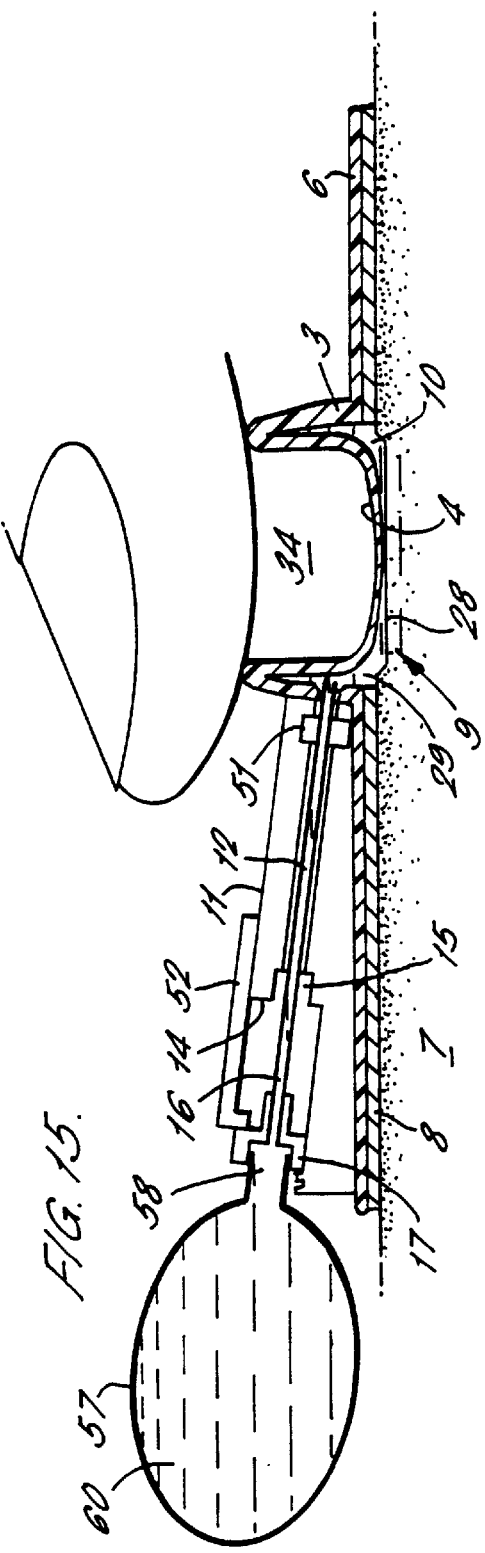

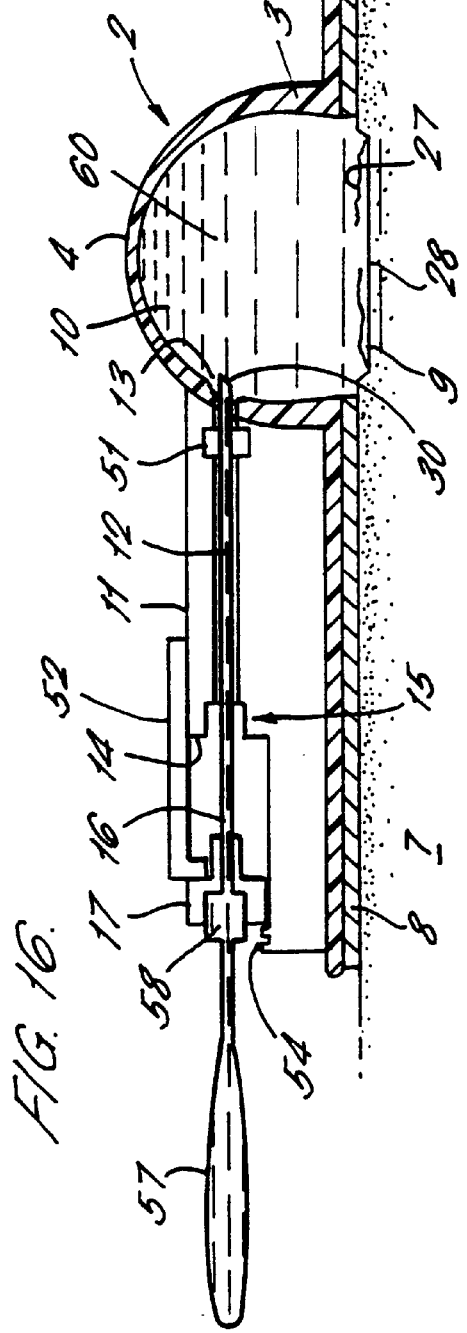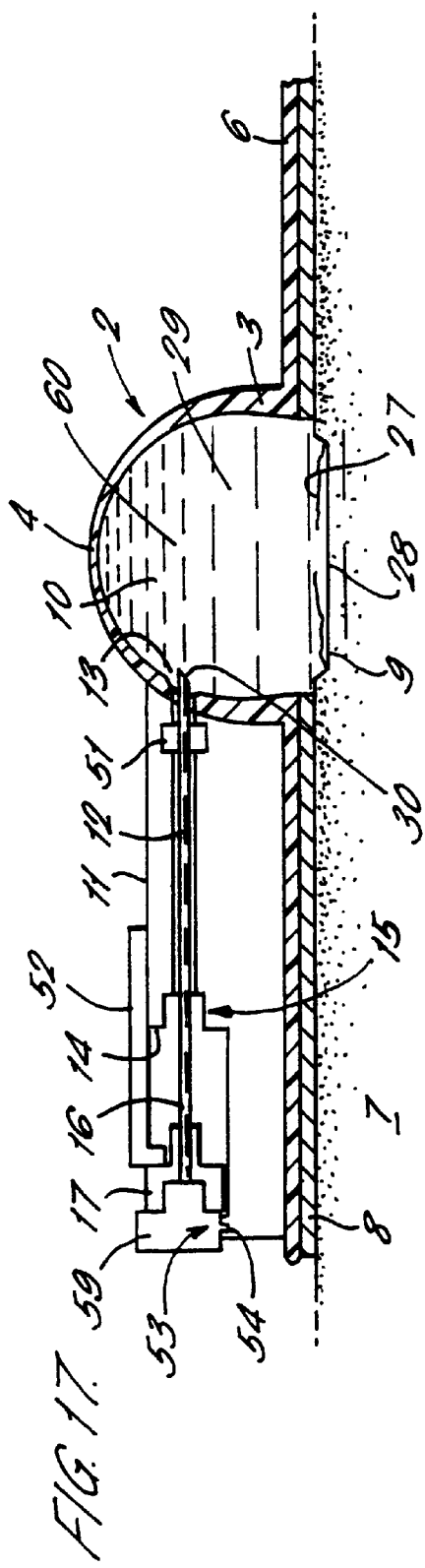

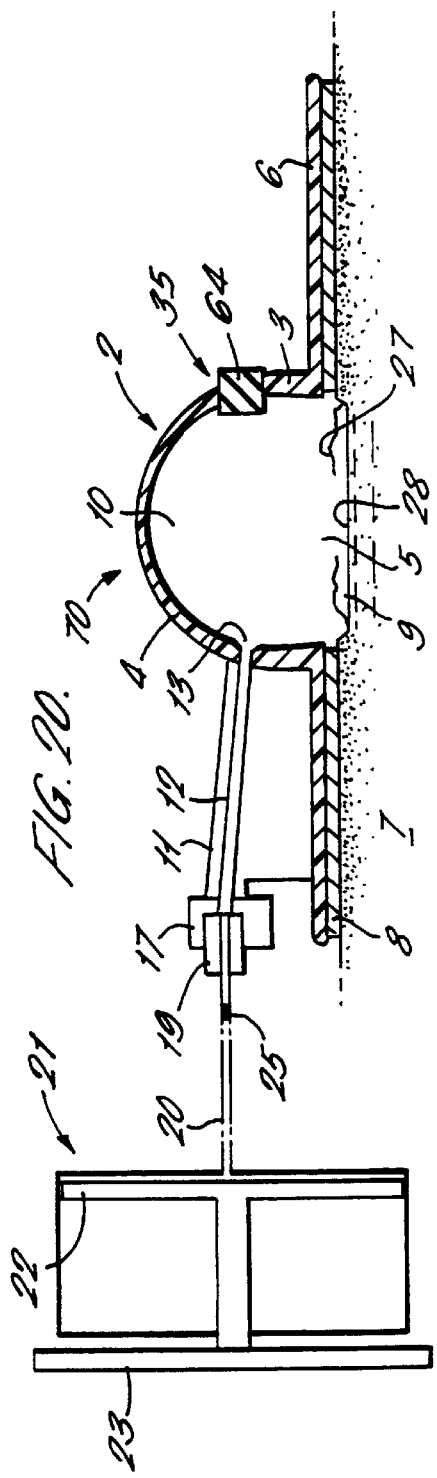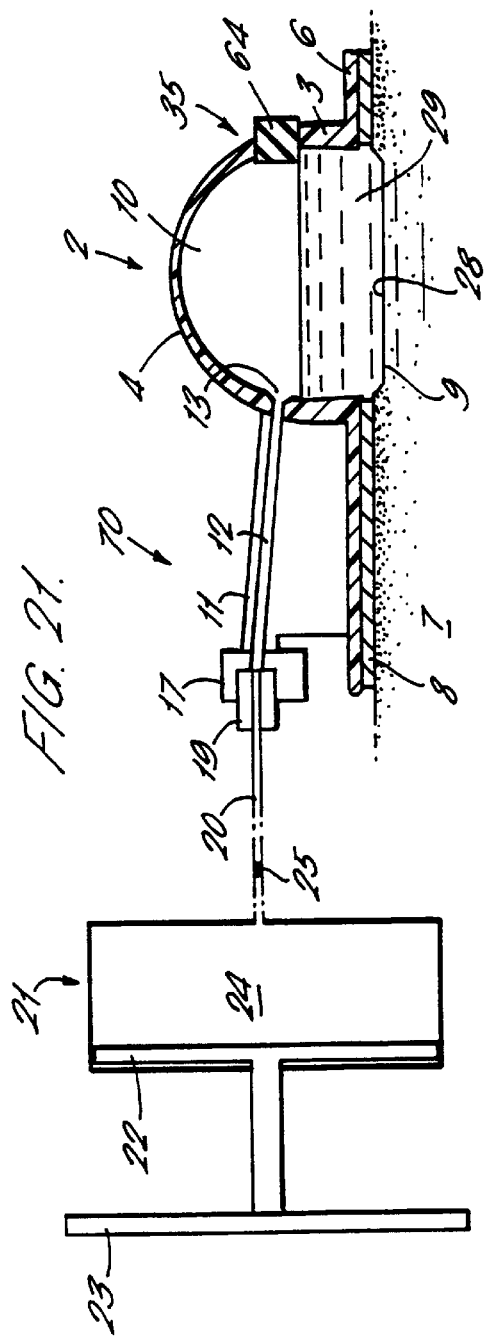

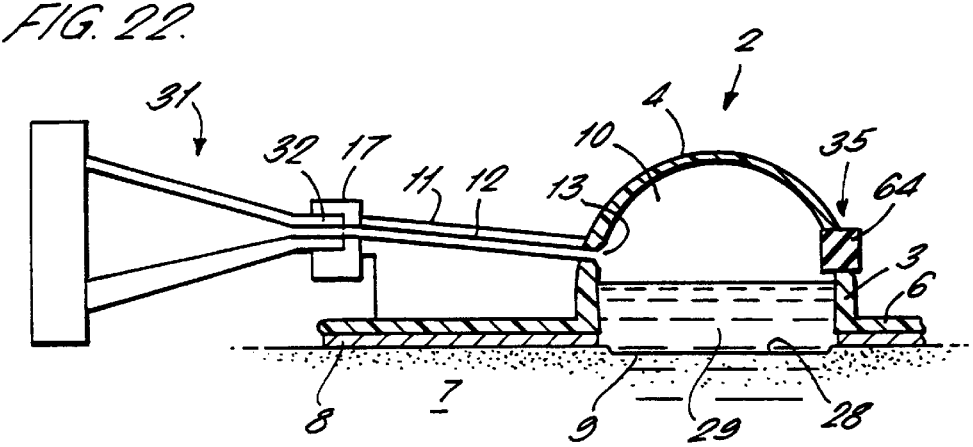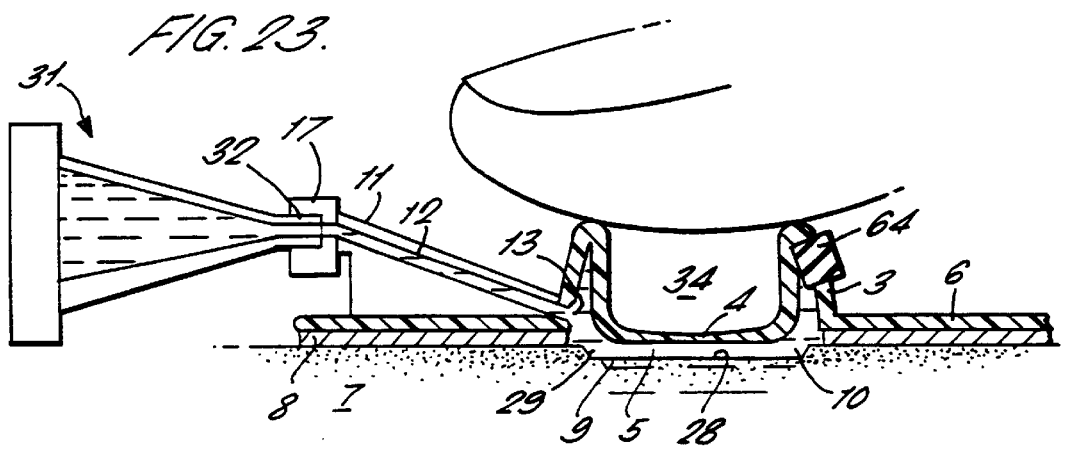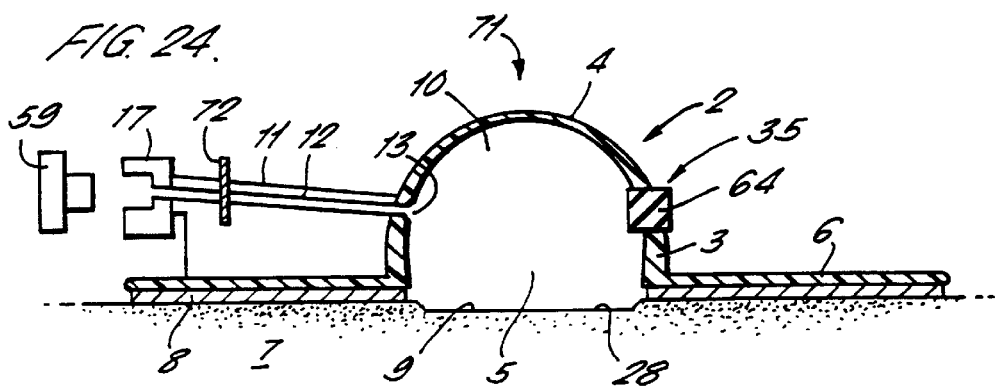

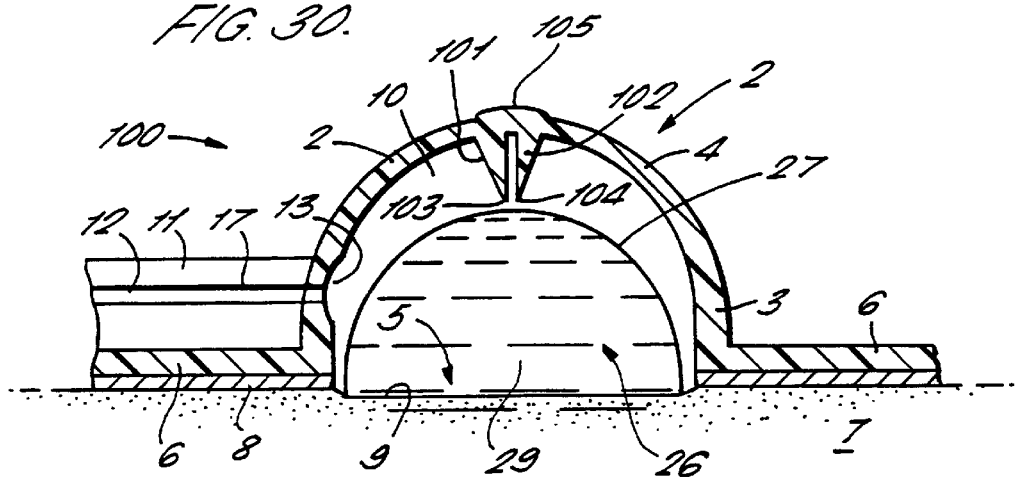
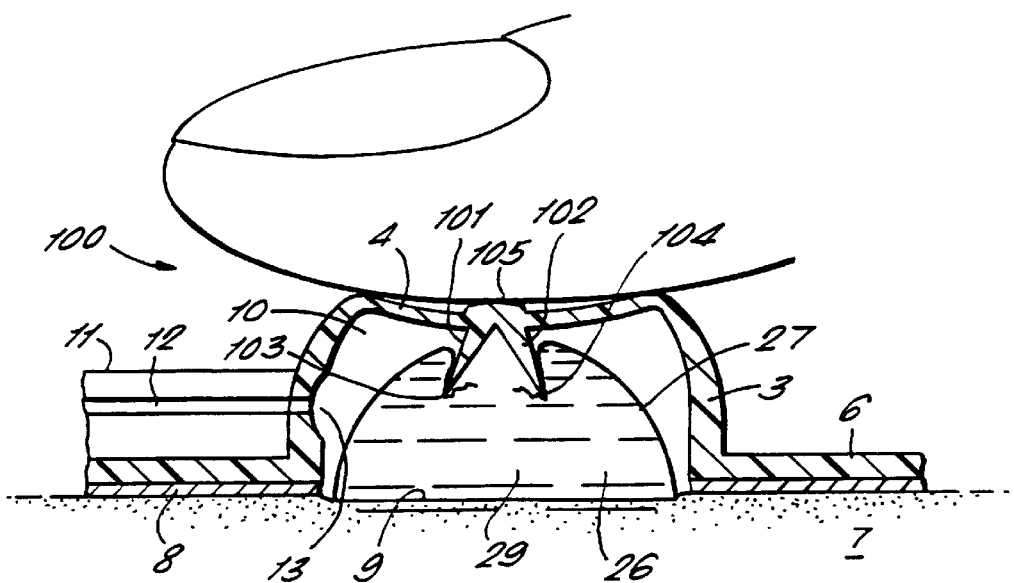

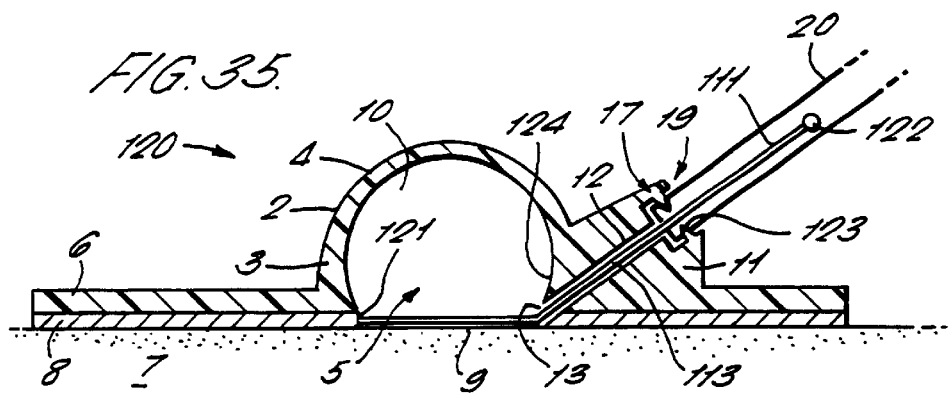
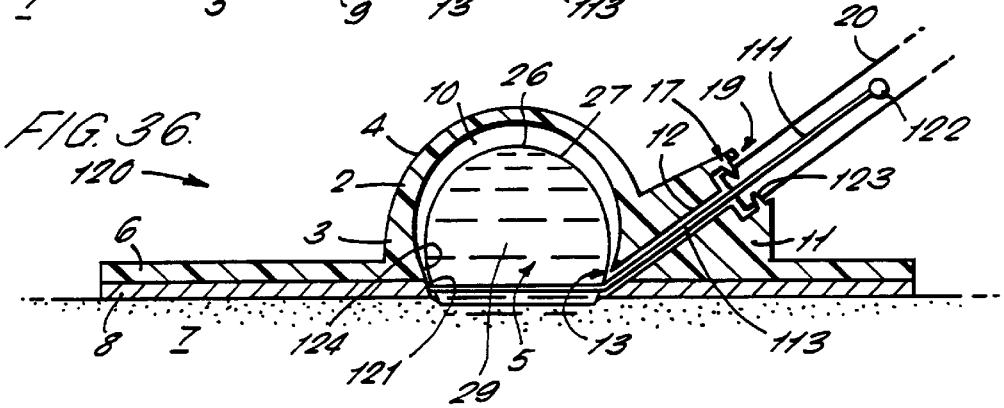
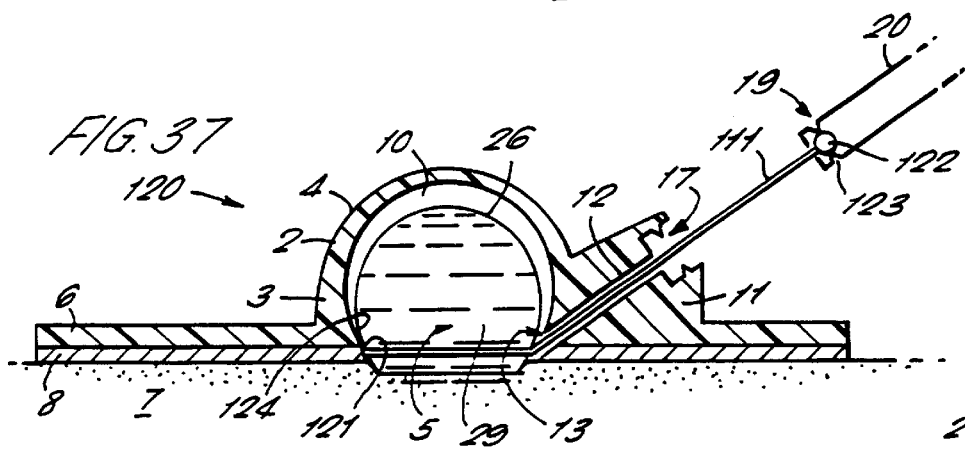
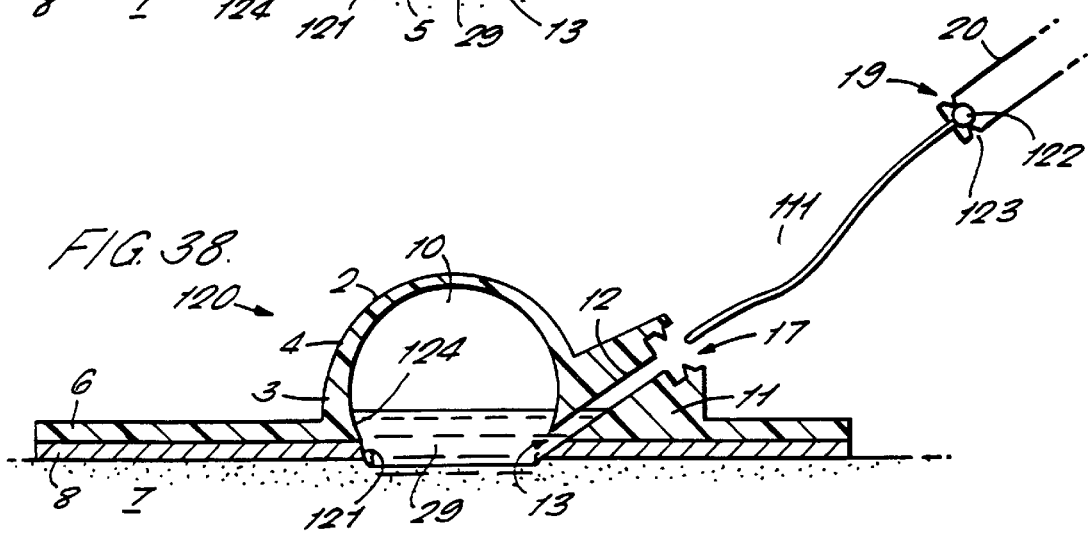

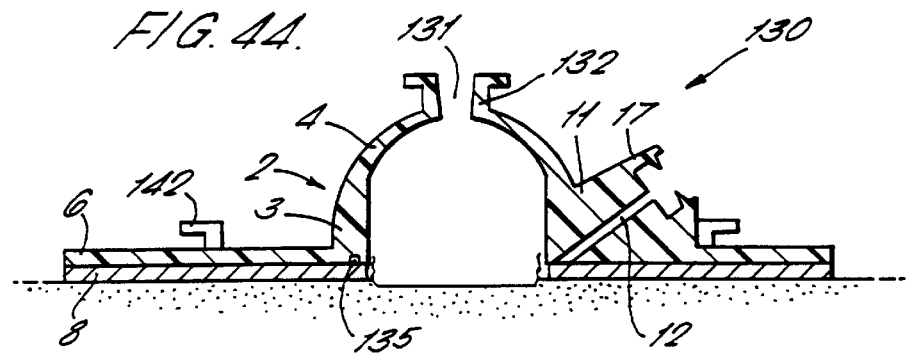
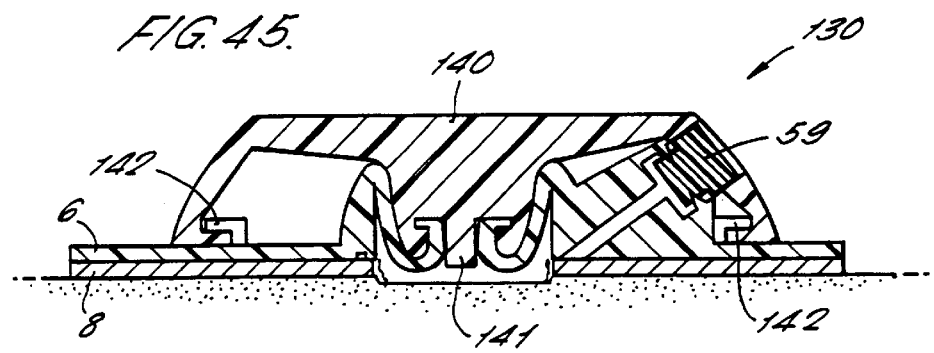
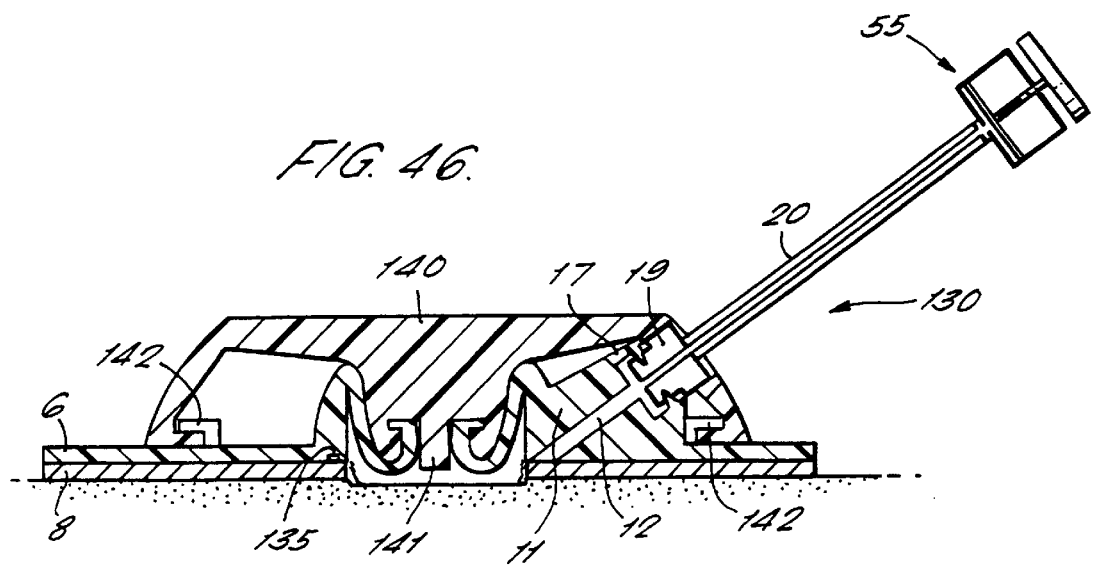

SUCTION BLISTER SAMPLING

This invention relates to apparatus for use in sampling fluids from the human or animal body using a suction blistering technique and to a method of sampling using such apparatus.

It is a known laboratory technique to form a suction blister on an area of skin by applying a suction cup to the skin within which a partial vacuum is sustained for a period of about two to three hours, the resulting suction blister resulting from the accumulation of a clear liquid plasma filtrate beneath an area of epidermis which becomes detached during this period from the underlying dermis of the skin. This detached area of epidermis forms a blister roof which can be painlessly opened or removed to gain access to the plasma filtrate and the plasma filtrate may then be sampled for analysis. Removal of this area of epidermis creates a standardised skin erosion. Plasma filtrate will continue to be generated at the exposed dermis (so long as dehydration and crust formation is prevented) so that by collecting and sampling this plasma filtrate, repeated or continuous analysis may continue over a period of time before the dermis becomes covered with a fresh epidermal layer as a result of the natural healing process.

Sampling and analysing such plasma filtrate has been shown to be an effective and minimally invasive alternative to other forms of sampling body fluids such as the use of implanted perforate tubes or intravenous cannulas.

This technique is particularly suited to analytic methods requiring only small quantities of sample fluids.

According to the present invention there is disclosed apparatus for use in a suction blister technique of sampling fluid from the human or animal body, the apparatus comprising a cup defining a chamber and having a rim portion defining an aperture communicating with the chamber, an annular flange extending outwardly from the rim portion whereby in use the flange is sealingly attachable to the body such that an area of skin closes the aperture, and a ducted portion connected to the cup and defining a duct communicating with the chamber, the cup further comprising a roof merging with the rim portion and formed of resiliently deformable material having a shape memory urging the roof into an expanded configuration in which the roof is held clear of the aperture and wherein the roof is deformable into a collapsed configuration in which the roof is proximal to the aperture.

An advantage of such apparatus is that the cup may remain in place during both the formation of a suction blister, the opening of the suction blister and subsequent sampling of plasma filtrate, thereby simplifying overall the procedure of obtaining a sample. The deformation of the roof of the cup between the expanded configuration and the collapsed configuration may be utilised to displace plasma filtrate from the chamber for the purpose of sampling, the plasma filtrate being expelled through the duct.

A further important advantage is that the size and shape of the chamber is selectively adaptable firstly to allow sufficient room for the growth of a suction blister while the roof is in the expanded configuration and secondly to restrict to a minimum the dead space volume during subsequent extraction of plasma filtrate when the roof is in the collapsed configuration. It is therefore not necessary to replace the suction cup used for formation of the suction blister with a separate apparatus with minimal chamber volume for use in sampling plasma filtrate.

The advantage of enabling the chamber volume to be minimised during sampling plasma filtrate arises from the relatively slow rate at which plasma filtrate continues to be generated at the skin erosion formed by removal of the epidermis from the underlying dermis, it being desirable to minimise the dead space volume within any collecting chamber, particularly when continuing to take samples for analysis over a period of time, either by allowing the plasma filtrate to progressively flow from the duct unaided or when the rate of production of plasma filtrate is enhanced by the application of suction.

The duct preferably communicates with the chamber via an access port which may conveniently be defined in the rim portion and the ducted portion may project outwardly from the rim portion and be formed integrally with the flange.

Locating the access port in the rim portion ensures that the access port through which plasma filtrate may be extracted from the chamber is in the immediate vicinity to the exposed dermis from which the plasma filtrate forms. This location is also advantageous in that collapsed configuration of the roof since it ensures that the access port continue to communicate with the reduced volume of the chamber.

Preferably the flange is provided with an adhesive layer operable in use to sealingly secure the flange to the body.

Other means may alternatively be used to sealingly secure the flange, such as for example use of straps binding the flange in intimate contact with the skin, preferably including annular grooves on the underside of the flange to enhance sealing action.

The apparatus may comprise a hollow needle which is longitudinally and slidably received in the duct so as to be movable longitudinally between a retracted position in which an innermost end of the needle is retracted from the chamber and an advanced position in which the innermost end projects into the chamber.

The hollow needle may thereby be used to disrupt the detached epidermis constituting the roof of a suction blister simply by moving the needle into the advanced position to rupture the detached epidermis and then retracting the needle. Plasma filtrate released by disrupting the detached epidermis may then be extracted via the hollow needle.

Conveniently the needle comprises a connector mounted at an outer end of the needle for coupling a co-operating connector in fluid communication with the chamber via the hollow needle.

The use of such a connector thereby enables a suction device initially to be coupled to the hollow needle to apply suction to the chamber during the formation of a suction blister and subsequently for the connector to be used to couple an analysing apparatus to the needle for receiving plasma filtrate.

The apparatus may comprise locking means operable between the needle and the ducted portion for locking the needle in the retracted position.

Such locking means has the advantage of ensuring that the needle does not become accidentally moved into its advanced position before completion of the formation of a suction blister.

A seal may advantageously be located in the duct so as to be penetrated by the needle. This is particularly important during the maintenance of suction within the chamber via the hollow needle.

Alternatively, the hollow needle may be a sliding fit within the duct of sufficient tightness to ensure an airtight seal.

As an alternative to the use of a hollow needle, the apparatus may comprise a connector formed integrally with the ducted portion and operable to couple a co-operating connector in fluid communication with the chamber via the duct.

The connector may therefore be connected initially to a source of suction in order to apply a partial vacuum within the chamber during the suction blister forming period and may subsequently be replaced by connection of an plasma filtrate collecting or analysing device.

Disruption of the suction blister may conveniently be achieved by incorporating in the cup a side port communicating with the chamber and closed by a septum which is penetrable in use by a needle and which is self healing on withdrawal of the needle.

Alternatively, the roof may be provided with blister disrupting formations projecting into the chamber.

This removes the need to provide any needle to disrupt the detached epidermis of the suction blister.

Conveniently the blister disrupting formations comprise first and second teeth having respective first and second pointed ends located adjacent one another when the roof of the cup is in the expanded configuration and which progressively move apart when the roof is being deformed into the collapsed configuration.

The teeth thereby have the advantage of being automatically moved into penetrating engagement with the detached epidermis and by moving apart they subsequently effect a tearing action to disrupt the detached epidermis.

Advantageously the roof of the cup comprises an external projection located in registration with the blister disrupting formations.

This has the advantage of enhancing the extent to which the formations are advanced during manual depression of the roof of the cup and further ensures that the external surface of the cup roof rapidly assumes a concave configuration which tends to improve the extent to which the pointed ends move apart.

Disruption of the suction blister may alternatively be accomplished by means of apparatus comprising a thread extending into the chamber and having an end portion extending externally of the chamber whereby the thread may be withdrawn in use from the chamber in a manner which disrupts a suction blister formed therein.

The thread, which may be any suitable cord, wire or ligature has the safety advantage of providing cutting action without the use of any sharp pointed feature being presented in proximity with the exposed dermis.

Preferably the thread comprises a loop portion extending in an initial position peripherally within the chamber so as to encircle the aperture whereby in use the withdrawal of the thread from the chamber is accompanied by the aperture being traversed by the loop portion in a garotting motion.

An advantage of such a loop portion is that there is no free end of the thread located within the chamber and the encircling motion ensures that the suction blister is fully engaged by the thread during withdrawal.

Conveniently the loop portion is detachably held in an initial position by adhesive at a location peripheral to the aperture.

Alternatively the loop portion may be detachably retained in the initial position by thread retaining means operable to apply a retaining force to the loop portion during withdrawal such that the retaining force acting on elements of the loop portion varies according to the elements initial displacement from the exit point at which the end portion exits the chamber, the variation in retaining force being selected to maintain tension in the loop portion during withdrawal.

An advantage of such an arrangement is to ensure clean cutting action by maintaining tension in the loop portion of the thread such that during withdrawal a linear portion of the loop portion traverses the aperture and sweeps across the aperture with a cutting motion.

The thread retaining means may comprise a groove defined in the flange and having a depth which decreases with increasing displacement from the exit point. The loop portion may thereby be retained in the groove in the initial position. During withdrawal, the element of the loop portion furthermost from the exit point will be the first to leave the groove to constitute the linear portion which traverses the aperture.

Alternatively the thread retaining means may comprise a plurality of circumferentially spaced lugs, the size of the lugs decreasing with increasing displacement from the exit point, each lug being operable to apply a retaining force to the loop portion which varies according to the size of the lug.

Preferably the end portion of the thread extends from the chamber via the duct. The end portion may then be connected to a suction tube releasably connected to the ducted portion to apply suction to the chamber via the duct and whereby the thread may be withdrawn from the chamber by withdrawal of the tube from the ducted portion.

This has the advantage of automatically achieving disruption of the suction blister at the time of disconnecting the suction tube from the ducted portion.

The end portion may be connected to an actuator piston which is slidable in an actuator cylinder releasably coupled to the ducted portion whereby the loop portion may be withdrawn from the chamber by retracting the actuator piston to a position in the actuator cylinder at which the duct remains closed to ambient air.

An advantage of such apparatus is to allow the loop portion to be withdrawn, thereby disrupting the suction blister by cutting through the detached epidermis, while at the same time continuing to maintain suction within the chamber.

Conveniently the duct extends at an acute angle relative to the flange such that the access port is located proximal to the junction of the rim and the flange.

This has the advantage of allowing the loop to be drawn from the chamber at a location which is as close as possible to the base of the suction blister i.e. to the dermis.

Advantageously the rim portion has an internal surface which tapers inwardly in a direction towards the aperture.

Such an arrangement tends to shape the suction blister, which would otherwise assume a hemispherical shape, so as to have a waist at its base. The loop of thread thereby encircles the base of the suction blister with a diameter which is less than the full width of the blister. Consequently the loop is captively retained so as to encircle the base of the suction blister during withdrawal of the loop from the chamber.

The thread may alternatively extend from the chamber via an exit hole formed separately from the access port and further provided with sealing means providing an airtight seal between the thread and the cup and operable to seal the exit hole after withdrawal of the thread.

In such an arrangement, the end portion of the thread may conveniently be releasably secured to the flange by adhesive.

Apparatus in accordance with the present invention may conveniently include a rim portion which is relatively less deformable than the roof whereby in the collapsed configuration of the roof the rim portion remains upstanding from the flange and the roof adopts a re-entrant shape extending through the rim portion.

Such an arrangement helps to minimise the dead space remaining within the chamber in the collapsed configuration of the roof.

Preferably the apparatus further comprises retaining means operable to retain the roof in the collapsed configuration.

The retaining means may conveniently comprise a plug received in a recess defined by the re-entrant shape of the roof in the collapsed configuration.

The apparatus may comprise a supporting structure operable between the flange and the roof to maintain the roof in the expanded configuration and releasable connecting means operable between the supporting structure and the roof whereby the roof may be selectively disconnected from the supporting structure.

Such an arrangement avoids accidental collapse of the roof during the suction blister forming period and may be particularly advantageous where relatively high levels of suction are to be applied within the chamber.

The roof may in an alternative arrangement define a suction port and a suction port connector for releasable connection to a source of suction.

The suction port connector may typically comprise a luer connector.

In such an arrangement, roof retaining means may be provided to retain the roof in the collapsed condition during the extraction of extrudate, the roof retaining means comprising a stopper operable to sealingly close the suction port.

Conveniently such roof retaining means may comprise a plug having releasable fastening fittings operable between the plug and the flange.

Typically bayonet fittings may be used.

According to a further aspect of the present invention there is disclosed a syringe for use in applying suction comprising a piston reciprocatable in a cylinder to define a syringe chamber of variable volume, a screw actuator co-operable by screw action with the cylinder to retract the piston between an advanced position in which the volume of the syringe chamber is a minimum and a retracted position in which the volume is a maximum, and stop means operable during return movement of the piston by reverse actuation of the screw actuator to limit advancement of the piston at an intermediate position at which the volume of the syringe chamber is intermediate the maximum and minimum.

Such a syringe is convenient for applying an initial relatively high level of suction and subsequently an intermediate level of suction for use in a method described below.

According to a further aspect of the present invention there is disclosed a fluid coupling comprising a female connector defining a conically divergent throat and a co-operating male connector having a frusto conical surface fitting sealingly within the throat, the female connector comprising a hub portion defining an aperture for the flow of fluid, a first throat portion merging with the hub portion and a second throat portion merging with the first throat portion at a location distal to the hub portion whereby the first and second throat portions together define the conically divergent throat and wherein the first and second throat portions are formed of a relatively deformable material and a relatively rigid material respectively.

An advantage of such an arrangement is that the relatively deformable material of the first throat portion provides sufficient compliance to ensure intimate sealing contact with the frusto-conical surface of the male connector while the relatively rigid material of the second throat portion constitutes a rigid supporting collar. This arrangement has been found to be more effective in sustaining long term airtight connection between the male and female connectors.

According to a further aspect of the present invention there is disclosed a method of forming a suction blister comprising the steps of adhesively sealingly securing a suction cup to an area of skin such that a selected portion of skin is accessible to a chamber defined by the cup, applying an initial level of suction within the chamber during an initial time period and subsequently applying a reduced level of suction during a subsequent time period.

An advantage of applying the initial higher level of suction is to remove pockets of air trapped by the adhesive seal, the cup typically comprising a flange which is adhesively coated such that some air will be entrained between the flange and the skin during application.

Preferably the initial period is between two and five minutes and the subsequent time period is between two and three hours.

According to a further aspect of the present invention there is disclosed a method of forming a suction blister including the step of adhesively sealingly securing a suction cup to an area of skin such that a selected area of skin is accessible to a chamber defined by the cup, applying suction to the chamber defined by the cup, applying suction to the chamber for a period of about two to three hours such that a suction blister is formed in the chamber, and gradually equilibrating the pressure within the chamber to atmospheric pressure.

An advantage of gradually equilibrating the pressure is to avoid disocciation of the adhesive seal from the skin.

Preferably suction is applied to the chamber by means of a syringe movable in a cylinder to define a variable volume syringe chamber, including the step of gradually equilibrating pressure in the chamber by returning the piston to a position in which the syringe chamber volume is a minimum and limiting the rate at which the piston moves while returning.

Conveniently the rate of movement of the piston is limited by means of a screw actuator operable between the piston and the cylinder.

The presence of the screw actuator requires an operator to turn the actuator a number of times to achieve piston movement so that by selecting a suitable thread the rate at which the piston can be moved may be controlled.

According to a further aspect of the present invention there is disclosed a method of applying suction to a suction chamber and providing an indication of the volumetric displacement of air from the chamber over a subsequent suction period during which suction is maintained, the method comprising the steps of connecting a suction means in communication with the chamber via a transparent tube in which a slug of liquid is retained by virtue of adhesive and viscous properties of the liquid, operating the suction means during an evacuation period to apply a pressure differential across of the slug of liquid greater than a threshold value of differential pressure required to disrupt the slug of liquid by the formation of a channel allowing the through flow of air whereby air is partially evacuated from the chamber, applying a constant level of suction by operation of the suction means during the subsequent suction period, allowing the slug of liquid to become reconstituted during an initial portion of the suction period into one or more portions closing the tube, and observing displacement of the slug of liquid along the tube in response to pressure differentials resulting from changes in the volume of air in the chamber and which pressure differentials are less than the threshold value of pressure differential.

An advantage of the method is that the position of the slug of liquid remains substantially unchanged by the initial application of suction to cause partial evacuation of the chamber.

According to yet another aspect of the present invention there is disclosed apparatus for use in a suction blister technique of sampling fluid from the human or animal body, the apparatus comprising first and second cups, each cup defining a chamber and having a roof and a rim portion defining an aperture communicating with the chamber and an annular flange extending outwardly from the rim portion, a cutting device comprising cutting means mounted in a support member; and guide means associated with the flange of the first cup and slidably receiving the cutting device and the second cup; wherein the cutting device and the second cup are movable along the guide member such that the cutting means severs the first cup from its respective flange and the second cup assumes the position of the first cup.

An advantage of such an arrangement is that the apparatus can be made very compact, keeping the size of the blister formed to a minimum, whilst still being easy to manipulate in use.

In such an arrangement, the guide means may comprise a first pair of guide rails formed along opposite edges of the flange of the first cup.

Conveniently, the guide means may further comprise a second pair of guide rails releasably attached to the first pair.

Typically, the first pair of guide rails may comprise a pair of opposed L-section members formed on opposite edges of the flange of the first cup and the second pair of guide rails may comprise a plate having a pair of opposed L-section members along opposite edges.

Preferably, the second cup and the cutting device are moveable linearly along the guide means.

The cutting device is also preferably positioned between the first and second cups.

Advantageously, the cutting means comprises a cutting blade having a cutting edge angled at approximately 75° to 80° to the direction of movement of the cutting device along the guide means.

The apparatus may further comprise removable retaining means for preventing movement of the first and second cups and the cutting device along the guide means.

The retaining means may comprise frame means surrounding the guide means.

Advantageously, means may be provided to locate the second cup as it is moved into the position of the first cup.

The locating means may comprise co-operating abutment members on the guide means and the second cup.

According to another aspect of the present invention there is described a method of forming a suction blister and sampling fluid formed at the site of the blister, comprising the steps of adhesively sealingly securing a suction cup to an area of skin such that a selected portion of skin is accessible to a chamber defined by the cup, applying suction to the chamber for a period of time sufficient to form a blister in the chamber, equilibrating the pressure within the chamber to atmospheric pressure, severing the blister from the skin with a cutting device, moving the suction cup away from the blister site, moving a second suction cup into a position sealingly over the blister site such that the site is accessible to a second chamber defined by the second cup, applying suction to the second chamber to draw fluid from the blister site, equilibrating the pressure within the second chamber to atmospheric pressure and deforming the chamber to expel fluid therefrom.

BRIEF DESCRIPTION OF THE DRAWINGS

Preferred embodiments of the present invention will now be described by way of example only and with reference to the accompanying drawings of which:

FIG. 1 is a schematic sectioned elevation of apparatus in accordance with a first embodiment of the present invention, the apparatus being shown secured to an area of skin and with suction being applied within the chamber;

FIG. 2 is a schematic sectioned elevation of the apparatus of FIG. 1 showing the formation of the suction blister;

FIG. 3 is a schematic sectioned elevation of the apparatus of FIGS. 1 and 2 after the restoration of ambient pressure to the chamber;

FIG. 4 is a schematic sectioned elevation of the apparatus of FIGS. 1 to 3 showing disruption of the suction blister by advancement of a needle to penetrate the epidermis;

FIG. 5 is a schematic sectioned elevation of the apparatus of FIGS. 1 to 4 showing the needle in a retracted position following disruption of the suction blister;

FIG. 6 is a schematic sectioned elevation of the apparatus of FIGS. 1 to 5 showing the collapse of the roof of the cup and displacement of plasma filtrate from the chamber into a sampling device;

FIG. 7 is a schematic sectioned elevation of an alternative apparatus having a cup with a roof retained in a collapsed configuration by a retaining plug;

FIG. 11 is a schematic sectioned elevation of a further alternative apparatus applied to an area of skin, prior to the application of suction within the chamber;

FIG. 12 is a schematic elevation of the apparatus of FIG. 11 showing the disruption of a suction blister by advancement of a needle;

FIG. 13 is a schematic sectioned elevation of the apparatus of FIGS. 11 and 12 showing the needle in a retracted position;

FIG. 14 is a schematic sectioned elevation of the apparatus of FIGS. 11 to 13 showing the roof of the cup in a collapsed configuration and extraction of plasma filtrate into a syringe;

FIG. 15 is a schematic sectioned elevation showing the apparatus of FIGS. 11 to 14 connected to a supply of liquid;

FIG. 16 is a schematic sectioned elevation of the apparatus of FIGS. 11 to 15 showing the roof of the cup in an expanded configuration and filled with liquid;

FIG. 17 is a sectioned elevation of the apparatus of FIGS. 11 to 16 following closure of the duct with a plug;

FIG. 20 is a schematic sectioned elevation of FIGS. 18 and 19 to which a suction syringe is fitted after formation of a skin erosion at the site of a disrupted suction blister;

FIG. 21 is a schematic sectioned elevation of the arrangement of FIG. 20 showing the application of suction to the exposed dermis at the erosion and extraction of plasma filtrate into the chamber;

FIG. 22 is a schematic sectioned elevation of the apparatus of FIGS. 20 and 21 following removal of the syringe and connection of the duct to a sampling device;

FIG. 23 is a schematic sectioned elevation of the apparatus of FIG. 22 showing the roof of the cup in a collapsed configuration and plasma filtrate from the chamber displaced into the sampling device;

FIG. 24 shows a modified apparatus incorporating a bacterial filter in the duct;

FIG. 30 is a schematic sectioned elevation of a further alternative apparatus;

FIG. 31 is a schematic sectioned elevation of the apparatus of FIG. 30 during manual compression of the cup roof;

FIG. 35 is a schematic sectioned elevation of a further alternative apparatus in use prior to formation of a suction blister;

FIG. 36 is a schematic sectioned elevation of the apparatus of FIG. 35 in use after formation of a suction blister;

FIG. 37 is a schematic sectioned elevation of the apparatus of FIGS. 35 and 36 illustrating the disconnection of a suction tube from the apparatus;

FIG. 38 is a schematic sectioned elevation of the apparatus of FIGS. 35 to 37 showing the disruption of the suction blister;

FIG. 44 is a schematic sectioned elevation of the apparatus of FIGS. 39 to 43 after removal of the syringe;

FIG. 45 is a schematic sectioned elevation of the apparatus of FIGS. 39 to 44 showing the retention of the cup in a collapsed configuration by action of a retaining plug;

FIG. 46 is a schematic sectioned elevation of the apparatus of FIGS. 39 to 45 showing connection of a syringe for the extraction of plasma filtrate;

DETAILED DESCRIPTION OF THE INVENTION

Figure 8:
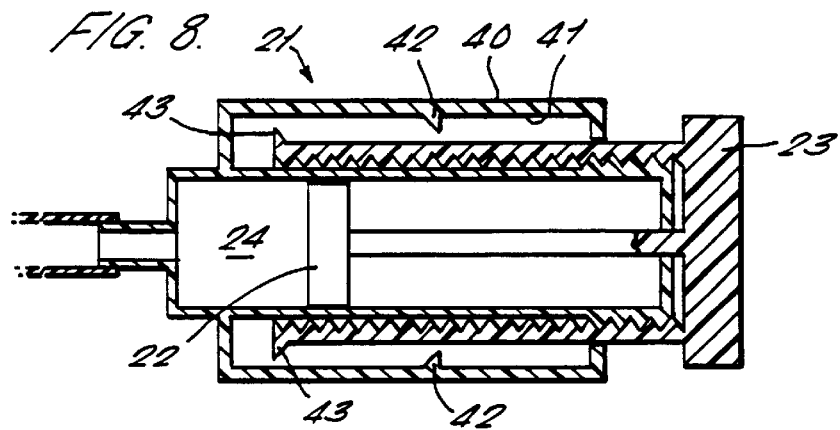
FIG. 8 is a sectioned elevation of a syringe for creating suction.

FIG. 1 shows an apparatus 1 in which a cup 2 is formed of a resiliently deformable plastics material having a shape memory such that in the absence of deformation it assumes a hemispherical shape as shown in the figure. The cup 2 thereby comprises an annular rim portion 3 which is peripheral to a roof 4 which is normally held clear of an aperture 5 defined within the rim portion 3.

The rim portion 3 merges at right angles with a flange 6 which is disc shaped and which is secured to the skin of a body 7 by means of an adhesive layer 8. The flange 6 and adhesive layer 8 extend around the complete circumference of the rim portion 3 so as to provide an airtight seal, an area of skin 9 of the body 7 being presented to the aperture 5 such that a closed chamber 10 is defined within the cup 2 and closed by the area of skin.

A ducted portion 11 formed integrally with the cup 2 extends radially from the rim portion 3 and attached to the flange 6. The ducted portion 11 defines a duct 12 communicating with the chamber 10 via an access port 13, a radially outermost end face 14 of the ducted portion having an outlet port 15 thereby accommodating a hollow metal needle 16 which extends through the duct 12.

The needle 16 is received as a sliding fit within the duct 12 with a sufficient tightness of fit to ensure an airtight seal therebetween.

The needle 16 terminates in a female connector 17 which is secured to an outer end 18 of the needle, the female connector accommodating a male connector 19 which is coupled to a tube 20. Suction may thereby be applied to the chamber 10 by means of a syringe 21 connected to the tube 20 and which thereby communicates with the chamber 10 by virtue of the in-line coupling of the tube 20 and hollow needle 16.

In FIG. 1 the syringe 21 is shown in a position in which its piston 22 has been fully retracted by action of a screw actuator 23, thereby creating suction within a cylinder 24 of the syringe. The apparatus 1 is shown schematically in FIGS. 1 to 3 and not to scale, the volume of the cylinder 24 being selected to be considerably greater than that of the chamber 10.

In use, the apparatus 1 is adhesively secured to the body 7 and the piston 22 is retracted by means of actuator 23 to apply suction within the chamber 10 and hence to apply suction to the area of skin 9 via aperture 5. The syringe 21 is arranged to have a capacity such that a partial vacuum of 400 millimetres of mercury below atmospheric pressure is exerted on the area of skin 9.

After an initial period of two to five minutes the piston 22 is adjusted in position to reduce the level of suction to about 200 millimetres of mercury below atmospheric pressure (generally no more than 250 millimetres of mercury).

A slug of liquid 25 is located within the tube 20 and will move in response to the displacement of air through the tube, thereby providing an indicator of the extent of displacement of air from the chamber 10 by suction.

Over a subsequent blister forming period of approximately two to three hours, the formation of a suction blister 26 typically occurs as shown in FIG. 2, the suction blister comprising a hemispherical detached area of the skin's epidermis 27 which is separated from the remaining dermis 28 of the skin by a volume of clear plasma filtrate 29.

As shown schematically in FIG. 2, the slug of liquid 25 will move in response to formation of the suction blister 26 by virtue of the displacement of air from the chamber 10 via the access port 13 as the volume of the blister increases.

At this stage, the partial vacuum in the chamber 10 is relieved at the end of the blister forming period in a gradual process in which the screw actuator 23 is reversed to move the piston 22 into its original position as shown in FIG. 3. This gradual equilibration of pressure in the chamber 10 to ambient pressure is desirable to avoid disruption of the adhesive seal between the flange 6 and the body 7, the equilibration process being preferably accompanied by the application of manual pressure to the flange. The syringe 21 is then disconnected by dissociating the male connector 19 from the female connector 17.

As shown in FIG. 4, the needle 16 is then advanced within the duct 12 by manual movement of the connector 17 by an operator so that an innermost end 30 of the needle projects into the chamber 10 and pierces the detached epidermis 27. The suction blister 26 is thereby disrupted allowing the plasma filtrate 29 to occupy the chamber 10.

As shown in FIG. 2, the existence of a partial vacuum in the chamber 10 results in a tendency for the dermis 28 to bulge slightly into the aperture 5. On release of the partial vacuum however as shown in FIGS. 3 and 4, the dermis 28 may relax to a position in which it is slightly recessed from the surrounding skin surface by virtue of the erosion of the area of skin by removal of the epidermis 27.

As shown in FIG. 5, the needle 16 may then be retracted by manual movement of the connector 17 to its original position so that the innermost end 30 of the needle no longer extends into the chamber 10 and is retracted within the duct 12 to a position in which it is spaced from the access port 13.

As shown in FIG. 6, a sampling device in the form of a cuvette 31 is then connected in communication with the hollow needle 16 by insertion of a further male connector 32 into the female connector 17. In order to displace plasma filtrate 29 from the chamber 10 into the cuvette 31, an operator applies a deforming force by finger pressure as shown in FIG. 6 to the roof 4 of the cup 2 such that the roof is deformed from its original expanded configuration as shown in preceding FIGS. 1 to 5 into a collapsed configuration as shown in FIG. 6 in which the roof is proximal to the aperture 5. In this collapsed configuration, the roof 4 assumes a re-entrant shape in which it projects into the chamber 10 thereby substantially reducing the volume of the chamber. The rim portion 3 remains upstanding from the flange 6, being partially stiffened by the presence of the ducted portion 11.

The roof 4 has a tendency to return to its expanded configuration by virtue of the shape memory of the material forming the cup 2. As shown in FIG. 7, the roof 4 may be held in its collapsed configuration by insertion of a plug 33 into a recess 34 created externally of the roof by its re-entrant shape in the collapsed configuration. FIG. 7 also illustrates a modification to the apparatus of FIGS. 1 to 6 in which an additional side port 35 is provided in the rim portion 3 and is overlayed by a resilient sealing member 36 which may be removed or pierced to gain access to the chamber via the side port when desired.

Following the displacement of plasma filtrate into the cuvette 31, the cuvette may be removed from the apparatus by disconnecting the connectors 32 and 17 and placing the cuvette in an analysing apparatus (not shown). Such cuvettes are typically provided with a capillary slot into which the plasma filtrate 29 is drawn by capillary action and with a reagent substance contained within the slot so that subsequent analysis by spectrographic or other means is readily facilitated in the analysing apparatus.

Figure 9:
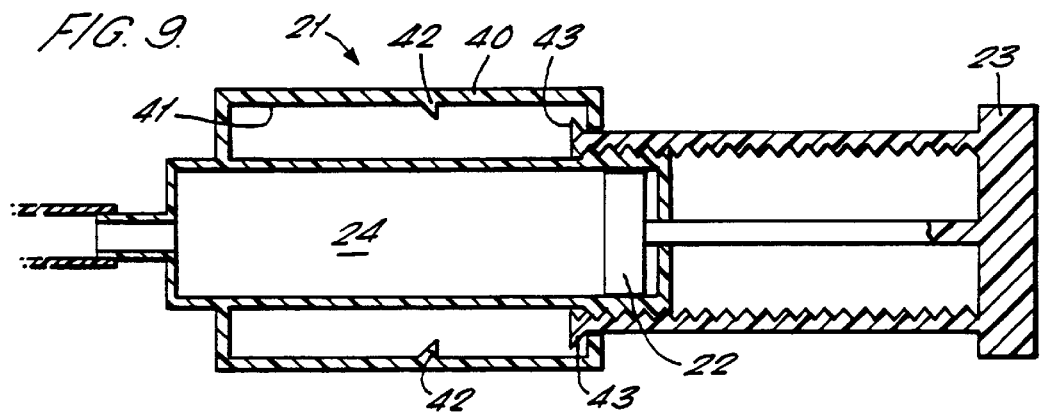
FIG. 9 is a sectioned elevation of the syringe of FIG. 8 showing a piston in a fully retracted position.
Figure 10:
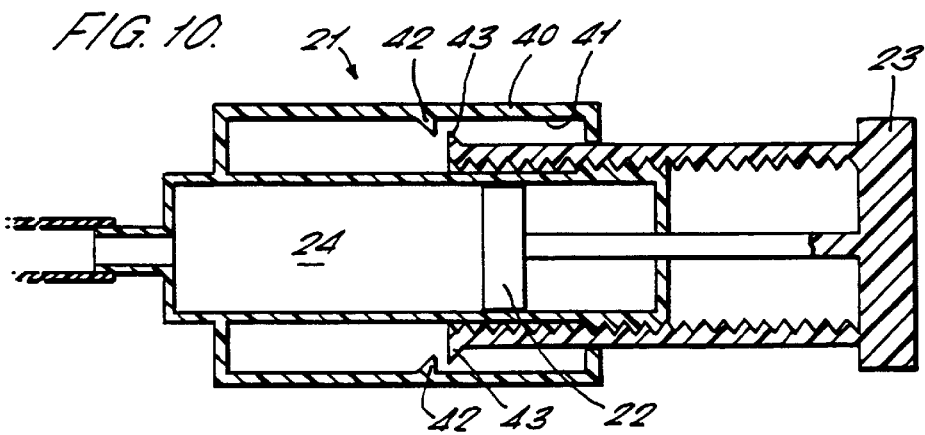
FIG. 10 is a sectioned elevation of the syringe of FIGS. 8 and 9 showing the piston in an intermediate position.

When the flange 6 is initially secured adhesively to the body 7 by means of adhesive layer 8, there is a tendency for pockets of air to be entrained and for this air to progressively bleed into the chamber 10 when suction is applied. In order to limit this effect, it has been found advantageous to initially apply a relatively high degree of partial vacuum for an initial interval and for the partial vacuum to be then relaxed to an intermediate level during a subsequent interval during the blister forming period. This adjustment in the level of suction may be readily accomplished using the syringe 21 of FIGS. 1 to 3 by means of the screw actuator 23 and the use of suitable positioning markers on the syringe. The procedure may however be simplified in a preferred embodiment of the syringe 21 as shown in FIGS. 8 to 10 in which the syringe 21 is provided with an outer casing 40 with an internal wall 41 from which stop formations 42 project so as to be engageable with co-operating formations 43 of the screw actuator 23. The screw actuator 23 is cylindrically formed so as to be screw threaded externally onto the cylinder 24 within which the piston 22 is reciprocatable to define a variable volume suction chamber. The stop formations 42 and co-operating formation 43 are tapered to provide ratchet action which will allow the co-operating formations to readily pass the stop formations when the piston 22 is being retracted but which will oppose advancement of the piston beyond the intermediate position.

The syringe 21 will therefore initially adopt the configuration shown in FIG. 8 in which the piston 22 is advanced within the cylinder 24 to a position in which the suction chamber of the syringe has minimum volume. Reverse actuation of the screw actuator 23 then allows the piston 22 to be progressively retracted to the fully retracted position shown in FIG. 9 in order to apply a relatively high degree of partial vacuum. Subsequent actuation of the screw actuator 23 in the opposite direction then advances the piston 22 as shown in FIG. 10 until the intermediate position is reached by engagement of the stop formations 42 and co-operating formations 43. Further advancement of the piston into the advanced position then requires more forceful actuation of the screw actuator 23 to enable the formations 43 to pass the stop formations 42.

The slug of liquid 25 is formed of a liquid which is inert, coloured, viscous, non-hydrous, non-toxic to the skin and which tends to adhere to the walls of the tube 20. A preferred material for the slug of liquid 25 has been found to be a hydrolysed starch coloured by means of a suitable dye (poly R478) and combined with a preservative agent to inhibit microbiological growth. A suitable preservative is Nipasol M (a Trade Mark) which consists of an aliphatic benzoic acid ester.

The use of such material for the slug of liquid 25 has been found to be satisfactory in that it exhibits a low rate of evaporation and has sufficient adhesion to the interior walls of the tube to prevent any major dislocation of the position of the slug of liquid within the tube when the piston is withdrawn. When the syringe 21 is initially actuated by retracting the piston 22, a rush of air through the tube is accommodated via the slug of liquid 25 by the formation of a central hole through the slug of liquid which tends to stretch out along the walls of the tube due to adhesion. After the initial rush of air, the air pressure on each side of the slug of liquid then equilibrates and the slug of liquid again reforms to close the tube, typically being separated into a number of fragments separated by air pockets.

The effect of this adhesion to the walls of the tube therefore allows the slug of liquid to remain substantially unmoved in position within the tube in response to the initial displacement of air when suction is applied by means of the syringe 21. If a sufficient pressure differential exists across the slug of liquid, the effect is to deform the liquid by elongation into a generally tubular shape thereby defining a central through-channel allowing the through flow of air. A through-flow of air from the chamber 10, via the tube 20 allows pressure to be equilibrated on either side of the slug of liquid during an evacuation period in which air is partially evacuated from the chamber. During a subsequent suction period in which a constant level of suction is applied by means of the syringe 21, surface tension effects in the liquid of the liquid slug result in the slug being reconstituted, typically as a number of spaced apart portions of the slug, each of which closes the tube 21 during an initial portion of perhaps five minutes of the suction period. The gradual displacement of air through the tube 20 in response to formation of the blister is however sufficiently slow to ensure that the slug of liquid moves along the tube in a manner which provides a measured indication of air displacement. This is because the pressure differential created across the slug of liquid due to the displacement of air from the chamber is typically much less than the threshold value of pressure differential required to disrupt the shape of the liquid slug to form a through-channel.

The precise composition of the liquid constituting the slug of liquid must be arrived at empirically. Performance is however critically dependent upon the internal diameter of the tube which should generally be in the range 0.1 to 3.0 millimetres.

In a particular example, the internal diameter of the tube is 0.9 millimetres with an external diameter of 2.5 millimetres, the tube being formed of flexible PVC (Isoflex—Trade Mark). The volume of the slug of liquid in this example is 25 micro litres and the liquid is hydrolysed starch mixed with dye and preservative as defined above.

Satisfactory adhesion and viscous properties can also be obtained using alternative materials, preferably other hydrophilic polymers such as dextrin, dextrin sulphate, hyaluronic acid and polyacrylic acid.

Glycerol may also be added to the liquid in a liquid solution of about 40%, glycerol being hygroscopic and thereby maintaining the overall water content of the liquid under conditions of normal air humidity. The glycerol also helps to prevent microbiological growth and thereby extends shelf life.

An alternative apparatus 50 is shown in FIG. 11 and will be described using corresponding reference numerals to preceding Figures where appropriate for corresponding elements. Apparatus 50 is shown schematically and not to scale, including a syringe 21 which may preferably be of the type shown with reference to FIGS. 8 to 10.

The apparatus 50 includes a cup 2 which is similar to the cup of the apparatus 1 in that it comprises a roof 4 merging with a rim portion 3 defining an aperture 5, the rim portion merging at right angles with a flange 6 which is secure to the body 7 by means of an adhesive layer 8.

The rim portion 3 is formed so as to have a greater thickness than the roof 4, thereby being somewhat stiffer in order to control the extent to which the rim portion remains upstanding during deformation of the roof 4 into the collapsed configuration referred to below with reference to FIGS. 14 and 15.

The apparatus 50 further comprises a ducted portion 11 defining a duct 12 communicating with the cup via an access port 13. A hollow needle 16 extends through the duct 12 and penetrates a rubber membrane 51 located in the duct 12 so as to provide an airtight seal between the needle and the internal wall of the duct 12.

The needle 16 projects from an outlet port 15 of the duct and terminates in a female connector 17. A locking member 52 is pivotally mounted on the ducted portion 11 so as to be movable between a stowed position as shown in FIG. 11 and a deployed position as shown in FIG. 13 in which it engages the female connector 17. The needle 16 is axially movable from the duct between a retracted position as shown in FIG. 11 and an advanced position as shown in FIG. 12 in which an innermost end 30 of the needle projects into a chamber 10 defined by the cup 2. As shown in FIG. 12, the advancement of the needle 16 into the advanced position may be used to disrupt a suction blister 26 as shown in FIG. 12 by piercing the detached epidermis 27.

When subsequently retracted into the position shown in FIG. 13, the needle 16 may then be locked in the retracted position by moving the locking member 52 into engagement with the female connector 17.

In use, as shown in FIG. 11, the syringe 21 is connected by means of a male connector 19 and a transparent tube 20 in line with the female connector 17 and the hollow needle 16 so that by actuation of the syringe the required degree of suction may be applied within the chamber 10 during a suction blister forming period, typically of about two to three hours.

During this blister forming period, the male connector 19 is retained in coupling engagement with the female connector by means of a catch 53 mounted on the male connector engaging a slot 54 formed on the ducted portion 11.

After formation of the suction blister 26, the pressure within the chamber 10 is gradually restored to ambient pressure before disconnecting the syringe 21 and advancing the needle 16 as shown in FIG. 12. After disrupting the blister 26, the needle is then retracted as shown in FIG. 13 so that plasma filtrate 29 from the suction blister then occupies the chamber 10.

Plasma filtrate may then be sampled in the manner described above with reference to apparatus 1 and FIGS. 6 and 7 to enable the plasma filtrate to be delivered to a cuvette 31 for subsequent sampling in an analysing apparatus.

As shown in FIG. 14, the extraction of plasma filtrate may alternatively be accomplished using a conventional syringe 55 having a male connector 19 connected to the female connector 17, withdrawal of a piston 56 of the syringe 55 being utilised to evacuate by suction the contents of the chamber 10 and to assist by the application of suction in the collapse of the roof 4.

As shown in FIGS. 15 and 16, the apparatus 50 may then be utilised following displacement of plasma filtrate 29 from the chamber 10 to transdermally deliver a drug 60 to the body by the admission of a liquid drug to the chamber 10, thereby allowing the drug to be transdermally delivered via the exposed dermis 28 in the absence of any intervening epidermis, the epidermis 27 having been delaminated from the dermis and subsequently ruptured during the suction blister forming process and disruption process using the needle 16.

Delivery of the liquid drug 60 into the chamber 4 may be accomplished in a variety of ways but in the example shown in FIGS. 15 and 16 a collapsible reservoir 57 having a male connector 58 is engaged with the female connector 17 while the volume of the chamber 10 is held at a minimum value by manually maintaining the roof 4 in its collapsed configuration. The roof 4 is then allowed to relax to its expanded configuration as shown in FIG. 16 by action of the resilience of the material forming the cup 2 and its inherent shape memory, this relaxation being responsible for an increase in volume of the chamber 10 thereby resulting in liquid drug 60 being drawn by suction into the chamber 10 from the reservoir 57. The male connector 58 may then be disconnected and replaced by a sealing closure member 59 as shown as FIG. 17 and which includes a catch 53 co-operable with the slot 54 so as to lock the closure member 59 in place. Escape of the liquid drug 60 from the apparatus 50 is thereby prevented by sealing action of the closure member 59.

The apparatus 50 may then be left in situ over an extended period of time during which transdermal delivery of the liquid drug 60 within the chamber 10 proceeds by a process of diffusion through the dermis 28. The rate of absorption of liquid drug 60 into the body 7 may if necessary be enhanced by applying positive pressure within the chamber 10 by the application of a deforming force to the roof 4, the diffusion process thereby being supplemented by convective absorption through the dermis 28.

As may be seen from a comparison of FIGS. 11 to 13 with the configuration shown in FIGS. 14 and 15, one consequence of the deformation of the roof 4 into the collapsed configuration is that the location of the access port 13 tends to be moved closer to the dermis 28. This effect, in combination with the reduction of the volume of chamber 10 to a minimum, enhances the suitability of the apparatus 50 to prolonged extraction of plasma filtrate 29 for sampling from the skin erosion formed at the site of the disrupted suction blister 26.

A further alternative apparatus 70 shown in FIG. 18 will now be described using corresponding reference numerals to those of preceding Figures where appropriate for corresponding elements.

The apparatus 70 differs from the apparatus 1 and 50 in that it is provided with a female connector 17 mounted integrally on the ducted portion 11 so as to provide direct communication with a duct 12 leading to chamber 10.

Figures 18, 19:
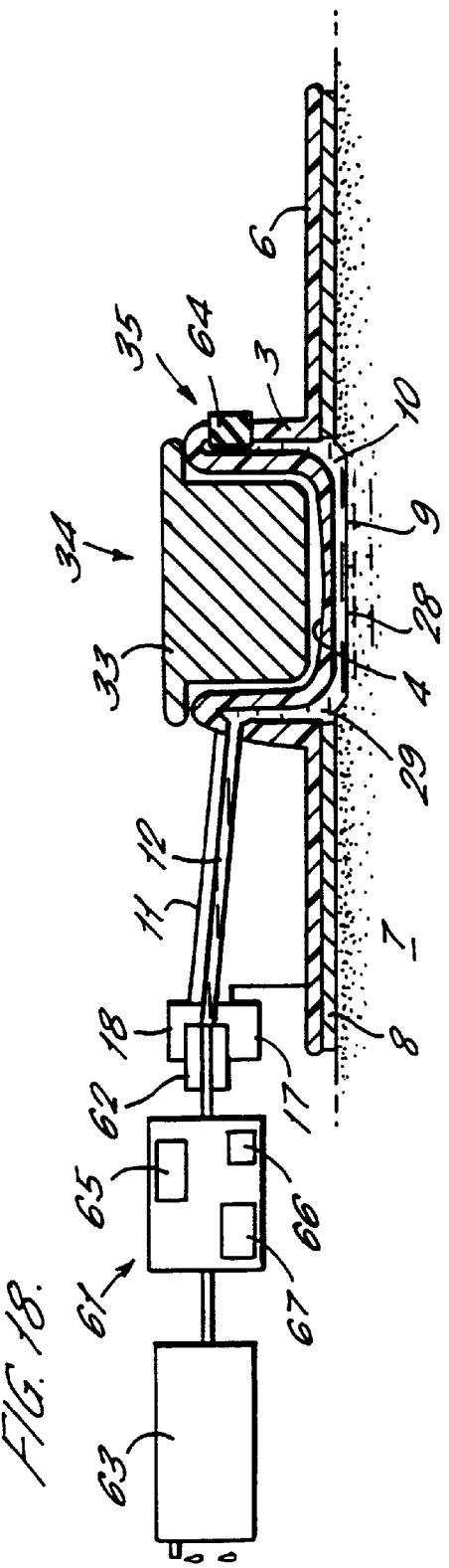
FIG. 18 is a schematic sectioned elevation of the apparatus of FIGS. 11 to 17 showing the roof of the cup in a collapsed configuration and retained by insertion of a retaining plug, the outlet of the duct being connected to an analyser.
FIG. 19 is a schematic sectioned elevation of the apparatus of FIG. 18 connected to a liquid delivery device.

As shown in FIG. 18, continuous monitoring and analysis of plasma filtrate 29 may readily be accomplished by connection of an analysing unit 61 to an outlet port 15 of the duct 12 by means of a male connector 62 engaging the female connector 17. As shown in FIG. 18, the roof 4 is preferably held in its collapsed configuration by insertion of a plug 33 into a recess 34 defined by the outer surface of the roof when it adopts a re-entrant shape relative to the chamber 10. Plasma filtrate 29 will continue to be generated via the exposed dermis 28 thereby tending to self generate a flow of plasma filtrate through the duct 12 into the analysing unit 61. The rate of flow can however be enhanced by connecting a suction pump 63 in series with the analysing unit 61 so that plasma filtrate is drawn through the analysing unit.

The effect of the suction pump 63 is therefore to provide negative pressure within the chamber 10 and this negative pressure enhances the rate at which plasma filtrate is produced via the dermis 28 thereby providing a further advantage. It is important that the roof 4 is sufficiently resiliently biassed into its expanded configuration to avoid collapse in response to this reduced pressure.

As shown in FIG. 18, the rim portion 3 may accommodate a side port 35 normally closed by an elastomeric septum 64. The rim portion 3 may alternatively by means of a sealing member 36 of the type described above with reference to FIG. 7.

The side port 35 may be used to introduce a cleansing liquid periodically into the chamber 10 for example by injection through the septum 64 or alternatively may be utilised to introduce to the chamber 10 substances for transdermal absorption through the dermis, to enhance or otherwise modify the production of plasma filtrate, or to delay the self healing of the erosion.

The analysing unit 61 may be a miniaturised electronic device suitable for attachment to the body 7 so as to allow the patient to remain ambulatory and the suction pump 63 may similarly be an electronically controlled micropump.

The analysing unit 61 in the example shown in FIG. 18 includes a digital display 65 providing an indication of status of the unit and the results of analysis and may further include an alarm light or buzzer 66 in order to indicate malfunction.

The analysing unit 61 will also include a sampling receptacle such as a cuvette or other device for the collection of plasma filtrate in a manner allowing the sample to be removed from the analysing unit for subsequent storage or further analysis.

The apparatus 70 does not include an equivalent to the needle 16 of the apparatus 1 and 50. Formation and disruption of the suction blister 26 may however be achieved first by connection of a suction pump or syringe 21 to the female connector 18 for the application of suction within the chamber 10 and subsequently by the insertion of the needle through the side port 35 so as to penetrate the septum 64 in order to pierce and thereby disrupt the detached epidermis of the suction blister. Subsequent withdrawal of the needle from the septum 64 results in the septum automatically re-sealing itself, the septum being formed of a suitable material such as rubber or silicone to achieve this effect.

As shown in FIG. 19, the apparatus 70 may be connected directly to a pumping device 68 incorporating a receptacle for storing plasma filtrate and having a male connector 69 engageable with a female connector 17 of the ducted portion 11. Such an arrangement may be preferred to the arrangement of FIG. 18 where continuous on-line analysis is not required. The cup 2 in this arrangement is shown with a roof 4 in its expanded configuration which may be preferred in certain circumstances where for example it is desired to increase the volume of the chamber 10 so as to accommodate a drug or a preparation for influencing the activity of the dermis. Injection of the drug or preparation is possible via the side port 35 which may also be used for the input of cleansing liquid.

The contents of the chamber 10 may then be emptied when required by manual depression of the roof 4 into the collapsed configuration in a similar manner to that shown in FIG. 15.

The apparatus 70 may alternatively be used as shown in FIGS. 20 to 23 where it is required to sample plasma filtrate 29 for analysis. FIG. 20 shows schematically the connection of a syringe 21 having a transparent tube 20 coupled to a female connector 17 of the ducted portion 11 by means of a male connector 19. A slug of liquid 25 contained within the tube 20 is visible, movement of the slug of liquid being indicative of displacement of air through the tube.

The situation shown in FIG. 20 is arrived at by first connecting the syringe 21 as shown and retracting the syringe piston 22 so as to apply suction within the chamber 10 during a blister forming period of approximately two to three hours. The piston 22 is then gradually advanced to equilibrate pressure within the chamber 10 with ambient pressure and the suction blister is disrupted by insertion of the needle (not shown) through the side port 35 by penetrating the self healing septum 64. The needle is then withdrawn leaving the disrupted epidermis 27 and plasma filtrate within the chamber 10. A sampling device such as a cuvette 31 may then be connected to the female connector 17 as shown in FIG. 22 and a sample of plasma filtrate 29 displaced from the chamber 10 into the cuvette by manual depression of the roof 4 as shown in FIG. 23, the roof 4 being inverted into its collapsed configuration in which the volume of the chamber 10 is reduced to a minimum.

Further samples of plasma filtrate 29 may then subsequently be required, for example in order to monitor levels of a component of the plasma filtrate over a period of time, and it may then be necessary to reconnect the syringe 21 to the apparatus 70 as shown in FIG. 21. In FIG. 21, the piston 22 is schematically shown in its withdrawn state and thereby applies suction within the chamber 10 which is shown in its expanded configuration of maximum volume. This application of suction within the chamber 10 enhances the rate at which further plasma filtrate 29 is produced at the exposed dermis 28 thereby enabling a fresh sample of plasma filtrate 29 to be produced within a relatively short time period immediately prior to the time at which the next sample is to be analysed. As shown in FIG. 21, a volume of plasma filtrate 29 occupies the lower part of the chamber 10 and the production of the plasma filtrate displaces air through the duct 12, this displacement being indicated by movement of the slug of liquid 25. The production of plasma filtrate 29 may also be viewed directly through the roof 4 if the apparatus 70 includes a cup formed of transparent plastics material.

This further sample of plasma filtrate 29 may then be extracted by first equilibrating pressure in the chamber 10 to ambient air by reversing the piston movement of syringe 21, disconnecting the syringe 21, and connecting the cuvette 31 to the female connector 17 as shown in FIG. 22. The sample of plasma filtrate 29 may then be extracted as shown in FIG. 23 by positive displacement from the chamber 10 as described above.

The apparatus 70 may be modified as shown in FIG. 24 where a modified apparatus 71 includes a filter 72 in line with the duct 12 and operable to prevent the ingress of bacteria to the chamber 10 via the duct while allowing the passage of air or liquid through the duct. A closure member 59 is provided to seal the female connector 17 when not in use.

Figure 25:
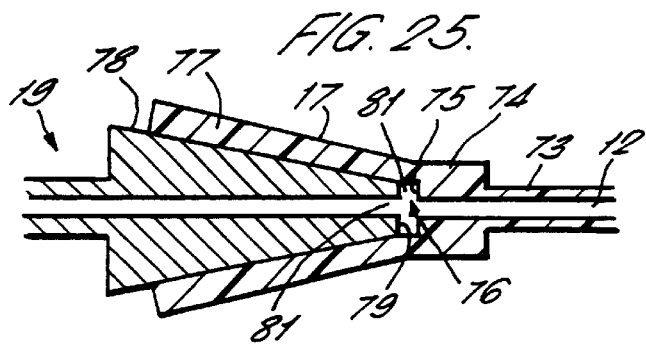
FIG. 25 is a sectioned elevation of a connector for achieving airtight coupling between the duct and a suction syringe.

In each of the above embodiments of the apparatus, the female connector 17 and male connector 19 are shown schematically. A preferred embodiment of the connectors 17 and 19 is shown in FIG. 25 where corresponding reference numerals to those of preceding Figures are used where appropriate for corresponding elements. In FIG. 25, a female connector 17 is connected to a ducted member 73 defining a duct 12.

The ducted member 73 may be a metal hollow needle of the type referred to above with reference to apparatus 1 or may for example be a ducted portion 11 of the apparatus 70 of FIG. 18 in which case the ducted member 73 is formed of plastics material and moulded unitarily with the female connector 17.

The female connector 17 comprises a hub portion 74 defining an end face 75 and which in turn defines an aperture 76 communicating with the duct 12.

A frusto conical portion 77 merges with the hub portion 74 so as to define a throat which diverges in a direction away from the hub portion.

The male connector 19 is shown inserted so as to occupy the volume of the throat and has a frusto conical surface 78 closely fitting in sealing engagement with the frusto conical portion 77. A leading end face 79 of the male connector 19 defines an opening 80 communicating with the duct 12 and, in the fully inserted position as shown in FIG. 25, remains spaced from the end face 75 of the female connector 17 such that an annular cavity 81 or dead space is formed.

Figure 27:
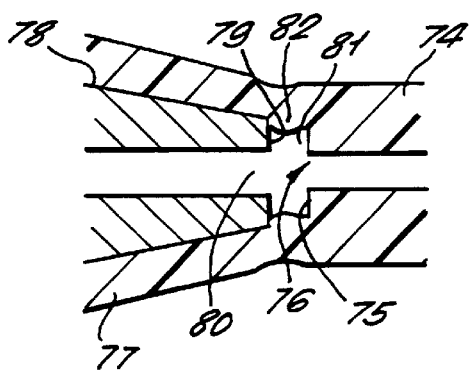
FIG. 27 is an enlarged sectioned elevation of the connector of FIG. 26.

The male connector 19 is formed of a relatively hard plastics material which is substantially non-deformable in use when inserted into the female connector 17. The female connector 17 however includes a relatively deformable material such that the frusto conical portion 77 deforms compliantly into intimate sealing contact with the frusto conical surface 78. As shown in detail in FIG. 27, the effect of suction applied within the duct 12 also results in a slight bulge of material 82 into the annular cavity 81 from the side wall of the frusto conical portion 77. The presence of this bulge 82 enhances the sealing action between the mating surfaces of the male and female connectors 19 and 17 thereby ensuring an airtight connection.

Figure 26:
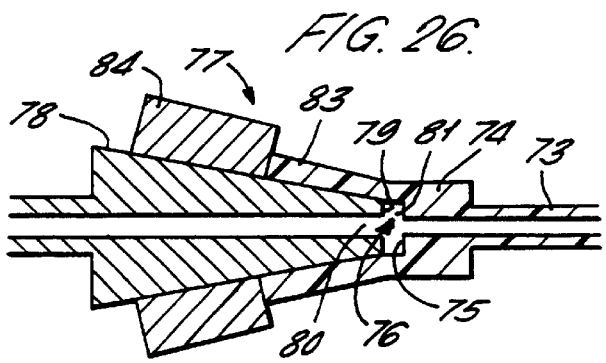
FIG. 26 is a sectioned elevation of an alternative connector.

An alternative configuration of the female connector 17 is illustrated in FIG. 26 in which the frusto conical portion 77 includes a first portion 83 of relatively deformable plastics material which merges with the hub portion 74 and a second portion 84 merging with the first portion 83 at a location distal to the hub portion, the second portion 84 being formed of a relatively rigid and non-deformable plastics material, preferably of the same type as the material forming the male connector 19.

The second portion 84 therefore constitutes a rigid collar at the entrance to the female connector 17 and which serves to provide rigid support between the male and female connectors when coupled. This arrangement has been found to be more effective in sustaining long term airtight connection between the male and female connectors 19 and 17 in use.

Figure 28:
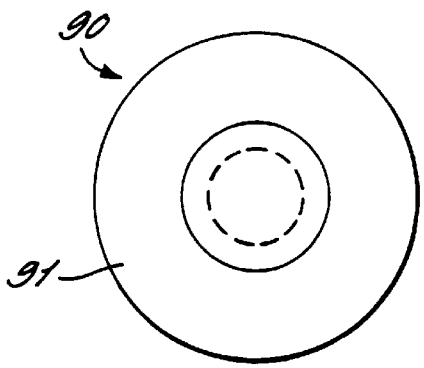
FIG. 28 is a plan view of a skin patch for covering the erosion after completion of sampling.
Figure 29:
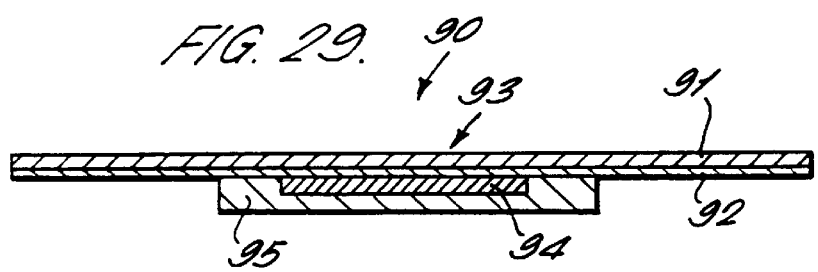
FIG. 29 is a sectioned elevation of the skin patch of FIG. 28.

FIGS. 28 and 29 illustrate schematically a skin patch 90 for use in covering the skin erosion after completion of the procedure using the above described apparatus 1, 50 or 70 and following removal of the apparatus by peeling off the flange 6 from the skin.

The skin patch 90 comprises a disc shaped air permeable film 91 which is secured to the skin by means of an annular adhesive layer 92 such that a central portion 93 overlays the exposed dermis 28 or skin erosion.

The central portion is provided with a pliable matrix 94 impregnated with silver chloride and which is contained within an absorbent porous dressing 95 presented to the skin at the side of the erosion.

A further alternative apparatus 100 is shown in FIGS. 30 and 31 and will now be described using corresponding reference numerals to those of preceding Figures where appropriate for corresponding elements.

The apparatus 100 comprises a cup 2 merging peripherally with a flange 6 secured to the skin by means of an adhesive layer 8. The cup 2 has a rim portion 3 which is relatively rigid and a deformable dome shaped roof 4 having a shape memory tending to keep the roof in an expanded configuration shown in FIG. 30 and being deformable into a collapsed configuration in similar manner to that described above with reference to the apparatus 1 in FIG. 6.

The apparatus 100 is further provided with a radially extending ducted portion 11 attached to the flange 6 and defining a duct 12 communicating with the chamber 10 defined within the cup 2.

Suction may be applied to the chamber 10 using a syringe as described above with reference to the apparatus 70 of FIG. 18 by connection of the syringe to a female connector of the ducted member 11. A suction blister 26 may thereby be formed in the chamber 10 by the prolonged application of suction during a blister forming period to an area of skin exposed to suction via an aperture 5 within the rim portion 3.

In order to disrupt the suction blister 26, the roof 4 is provided with first and second internally projecting teeth 101 and 102 which project centrally from the roof in a direction towards the aperture 5 in parallel spaced relationship when the roof is in its normal expanded configuration as shown in FIG. 30. The teeth 101 and 102 taper to provide pointed ends 103 and 104 respectively which in the expanded configuration of the roof are adjacent one another.

The roof 4 is also provided with an external projection 105 at a location opposite to the first and second teeth 101,102 such that, when manually depressed as shown in FIG. 31, the roof tends to rapidly adopt a concave shape in which the pointed ends 103,104 move apart while at the same time being displaced towards the aperture 5. This displacement and moving apart motion penetrates and disrupts the detached epidermis 27 of the suction blister 26 as shown in FIG. 31.

The alternative apparatus 100 therefore does not require the insertion of a needle in order to disrupt the suction blister in order to allow plasma filtrate 29 to occupy the chamber 10.

Figure 32:
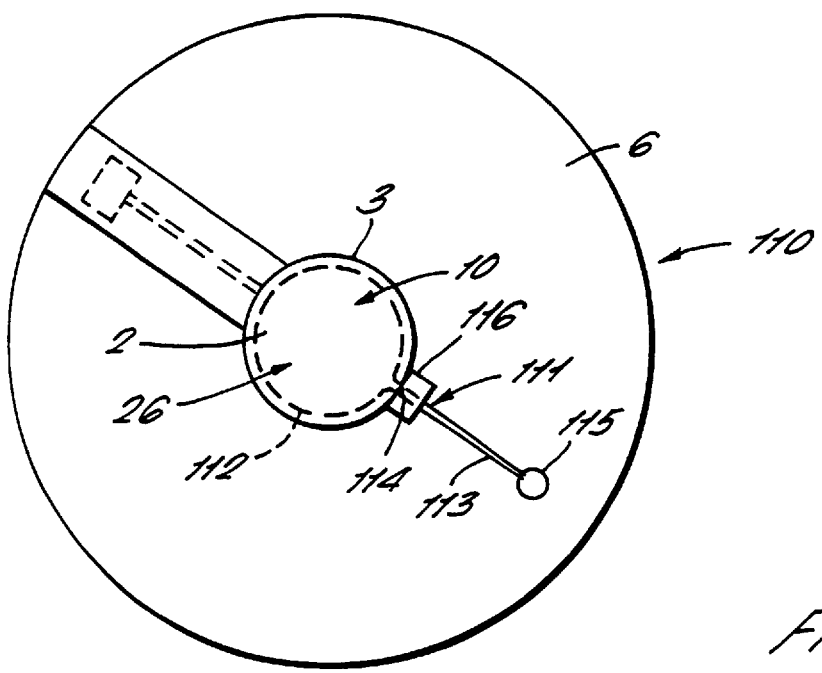
FIG. 32 is a plan view of a further alternative apparatus having a thread for disrupting a suction blister.

A further alternative apparatus 110 is shown in FIG. 32 and will now be described using corresponding reference numerals to those of preceding Figures where appropriate for corresponding elements.

The apparatus 110 comprises a cup 2 merging with a flange 6 as seen in plan view in FIG. 32, the cup defining a chamber 10 within which a suction blister 26 is formed in like manner to the suction blister 26 described above.

In order to disrupt the suction blister 26, the cup 2 is provided with a thread 111 having a loop portion 112 extending peripherally within the chamber 10 and having intertwined end portions 113 extending externally of the chamber 10 via an exit hole 114 defined in the rim portion 3 of the cup.

Figure 33:
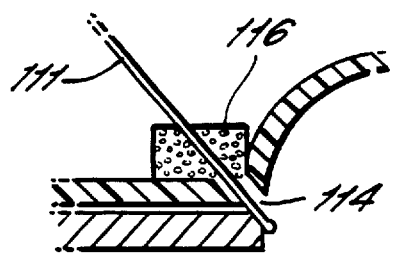
FIG. 33 is an enlarged detail of part of the apparatus of FIG. 33 shown in sectioned elevation.

As shown in FIG. 33, the loop portion 102 extends peripherally within the aperture 5 defined by the rim portion 3 at the junction between the flange 6 and the rim portion 3.

The end portions 113 terminate in a handle 115 which is externally accessible to the user.

The loop portion 112 is adhesively retained in situ during the blister forming period in which the suction blister 26 is formed in the chamber 10.

The exit hole 114 is sealed by a pocket of gel 116 arranged such that when the thread 111 is in situ the gel maintains an airtight seal between the thread and the cup and flange, the airtight seal also being retained when the thread 111 is removed by pulling the handle 115 such that the loop portion 112 is fully withdrawn from the chamber 10.

The suction blister 26 may thereby be disrupted by pulling the handle 115 such that the loop portion 112 encircling the suction blister is dislodged from its initial position and rapidly decreases in loop size so as to detach the epidermis 27 in a garotting motion.

Figure 34:
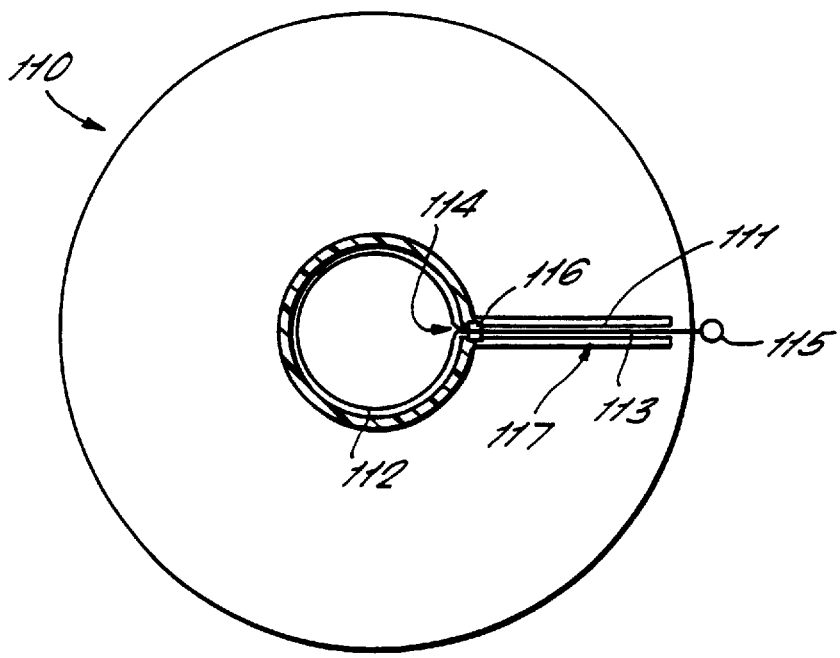
FIG. 34 is a plan view showing detail of the thread adhesively secured to the flange of the apparatus of FIGS. 32 and 33.
Figure 39:
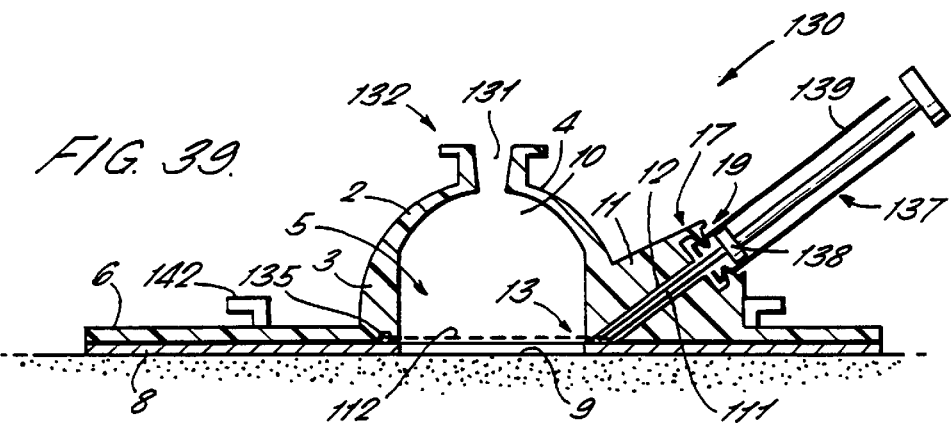
FIG. 39 is a schematic sectioned elevation of a further alternative apparatus.

The end portions 113 are held in position prior to use as shown in plan view in FIG. 34 by an adhesive strip 117 which extends radially along the upper surface of the flange 6.

The thread 111 may be formed of glass fibre, wolfram, gold or silver with a thickness of between 30 and 100 microns.

A further alternative apparatus 120 will now be described with reference to FIGS. 35 to 38 using corresponding reference numerals to those of preceding Figures where appropriate for corresponding elements.

The apparatus 120 is similar to the apparatus 110 of FIG. 32 in that it comprises a cup 2, a flange 6 with adhesive layer 8, and a thread 111 provided for the purpose of disrupting a suction blister 26. In the apparatus 120 however, the thread 111 extends through the duct 12 defined by ducted portion 11, the duct being provided primarily for the purpose of applying suction within the chamber 10 and subsequently facilitating the extraction of plasma filtrate 29.

As shown in FIG. 35, the apparatus 120 is initially applied to a body 7 using the adhesive layer 8 such that the chamber 10 is sealed by an area of skin 9 closing an aperture 5 of the chamber 10.

The ducted portion 11 is connected to both the flange 6 and the rim portion 3 so as to define the duct 12 at an acute angle relative to the plane of the flange selected such that the duct extends downwardly from a female connector 17 to an access port 13 communicating with the cup at the point of intersection between the rim portion 3 and the flange 6.

A tube 20 connected to a syringe (not shown) for the purpose of applying suction within the chamber and the tube has a male connector 19 which is initially coupled in an airtight manner to the female connector 17. The thread 111 has a loop portion 112 extending internally of the chamber 10 and peripherally of the aperture 5 and adhesively retained in this position by contact with an inner annular edge portion 121 of the adhesive layer 8.

An end portion 113 of the thread 111 extends through the duct and into the tube 20, terminating in an enlargement 122 which is captively retained within the tube by means of a restriction 123 formed at the male connector 19.

In use, the syringe is used to apply suction within the chamber 10 during a blister forming period in which a suction blister 26 develops and extends into the chamber. Growth of the blister 26 is observable through the roof 4 of the cup by virtue of the cup 2 being formed of a transparent plastics material.

The pressure within the chamber 10 is then gradually equilibrated to ambient pressure by de-actuating the syringe and the tube 20 is removed from the apparatus by disconnecting the male and female connectors 19 and 17 as shown in FIG. 37.

Separation of the tube 20 from the ducted portion 11 results in the end portion 113 being pulled, thereby dissociating the loop portion 112 from the adhesive layer 8 and progressively reducing the area of the loop as the thread 111 is drawn out of the chamber 10 via the duct 12.

Since the loop portion 112 encircles the suction blister 26, this garroting motion progressively disrupts the suction blister and dissociates the epidermis 27 from the area of skin so as to release plasma filtrate 29 into the chamber 10.

The tube 20 is finally removed entirely from the apparatus 120 by withdrawal of the tube 20, the thread 111 being fully withdrawn as shown in FIG. 38.

The plasma filtrate 29 may then be sampled by connection to the female connector 17 of sampling apparatus such as the cuvette 31 referred to above.

As shown in FIGS. 35 to 38, an internal surface 124 of the rim portion 3 tapers inwardly in a direction towards the aperture 5 so that, as shown in FIGS. 36 and 37, the suction blister 26 tends to adopt a similar shape in the vicinity of the rim portion such that the loop portion 112 of the thread 111 encircles the base of the suction blister with a diameter which is less than the full width of the blister. Consequently, when the end portion 113 is pulled as shown in FIG. 37, the loop portion 112 when dissociated from the adhesive layer still tends to encircle the base of the suction blister 26 rather than slipping over the top of the suction blister. The loop portion 112 thereby is constrained to remain in a position in which it encircles the suction blister, thereby ensuring that the subsequent garotting motion caused by pulling the tube 20 disrupts the suction blister by cutting through the base of the blister.

A further alternative apparatus 130 will now be described with reference to FIGS. 39 to 47 using corresponding references to those of preceding figures where appropriate for corresponding elements.

The apparatus 130 comprises a flange 6 defining an aperture 5 and having a cup 2 defining a chamber 10 for the application of suction to an area of skin 9.

The cup 2 has a rim portion 3 merging with the flange 6, the rim portion having a cylindrical internal wall and being formed with a greater thickness than the roof 4 of the cup 2.

A thread 111 extends through a duct 12 defined by a ducted portion 11, the duct 12 communicating with the chamber 10 via an access port 13 at the point of intersection between the rim portion 3 and the flange 6.

Figure 41:
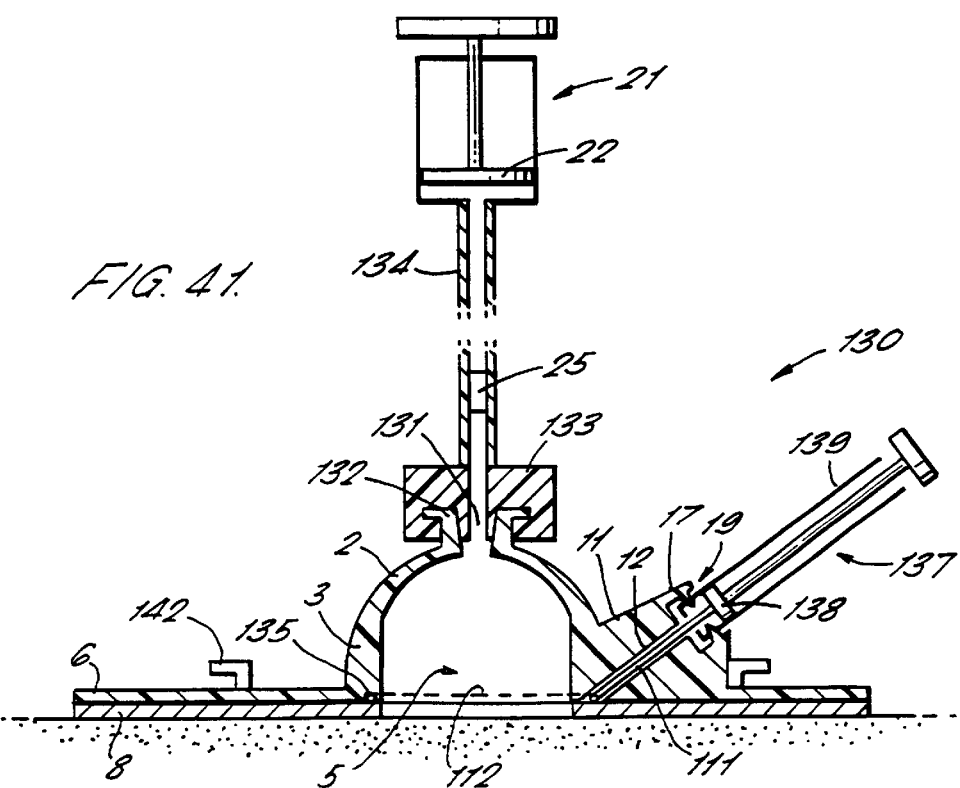
FIG. 41 is a schematic sectioned elevation of the apparatus of FIGS. 39 and 40 showing the connection of a syringe to apply suction within the chamber.

The cup 2 further defines a suction port 131 which is centrally located and in coaxial alignment with the cylindrical axis of the rim portion. The roof 4 of the cup 2 is integrally moulded with a female luer connector 132 allowing a co-operating male luer connector 133 as shown in FIG. 41 to make connection between the suction port 131 and a tube 134 through which suction may be applied to the chamber 10 by means of a syringe 21.

The thread 111 has a loop portion 112 which in its initial configuration as shown in FIGS. 39 to 42 extends peripherally of the aperture 5 and is received in a circular groove 135 which is provided in the lower face of the flange 6. The groove 135 is overlaid by the adhesive layer 8 which covers the lower face of the flange.

Figure 40:
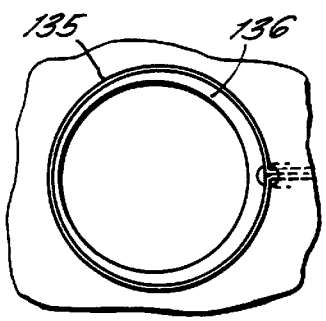
FIG. 40 is a partial plan view of the apparatus of FIG. 39 showing the location of a thread for disrupting a suction blister.

As shown in FIG. 40, the circular groove 135 has a centre which is offset from the centre of the aperture 5 in a direction towards the access port 13 so that the groove 135 may be regarded as bounded by an inner wall 136 which varies in thickness such that the thickness of the wall decreases progressively in a direction away from the access port 13.

The thread 111 has end portions 113 which extend from the loop portion 112 to an actuator 137 consisting of an actuator piston 138 to which the end portions 113 are connected and an actuator cylinder 139 within which the piston is sealingly slidable. The actuator cylinder 139 has a male connector 19 releasably coupled in sealing relationship with a female connector 17 of the ducted portion 11 so that the duct 12 communicates with the interior of the cylinder as far as the position of the piston 138.

The actuator 137 thereby allows the end portions 113 to be pulled by retracting the actuator piston 138 within the actuator cylinder 139 without unsealing the duct 12. This arrangement therefore makes it possible to utilise the suction blister disrupting properties of the thread 111 whilst still maintaining suction within the chamber 10.

As shown in FIG. 41, a syringe 21 is connected to the chamber 10 by means of the male and female luer connectors 132 and 133 and suction applied by retracting a piston 22 of the syringe 21 into a locked retracted position enabling suction to be maintained within a blister forming period.

Figure 42:
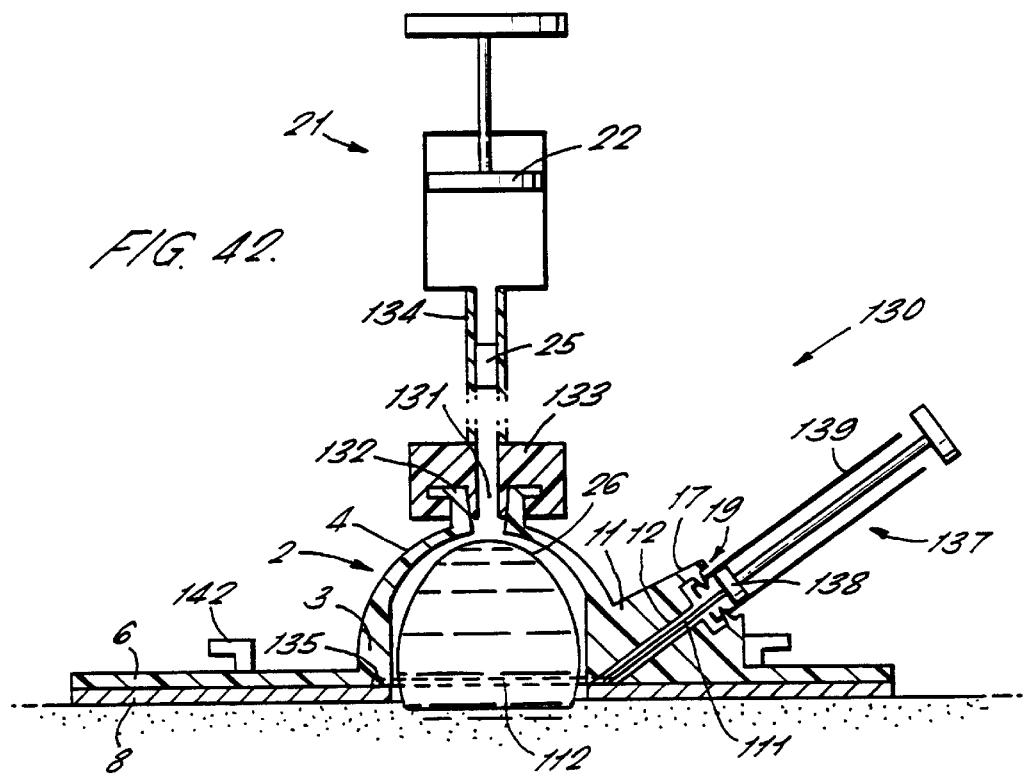
FIG. 42 is a schematic sectioned elevation of the apparatus of FIGS. 39 to 41 showing the formation of a suction blister in response to suction within the chamber.

FIG. 42 shows the formation of a suction blister 26. The tube 134 includes a slug of liquid 25 of a type described above for the purpose of providing an external indication of blister growth by virtue of movement of the slug of liquid in response to displacement of air through the tube.

In order to disrupt the suction blister 26, the actuator piston 138 of the actuator 137 is pulled such that the actuator piston begins to retract within the actuator cylinder 139 and the end portions 113 of the thread 111 are pulled through the duct 12. The loop portion 112 then becomes tensioned and tends to reduce the area bounded by the loop portion. The loop portion 112 progressively leaves the groove 135, beginning with that portion of the loop portion retained by the minimum thickness of wall 136 i.e that portion which is furthermost from the access port 13.

The effect of the progressively varying thickness of wall 136 is therefore to control the manner in which the loop portion 112 exits the groove 135 and in particular has the effect of maintaining the loop portion under constant tension. A linear portion of the loop portion 112 therefore traverses the aperture 5 and progressively sweeps across the aperture to cut the suction blister 26.

Figure 43:
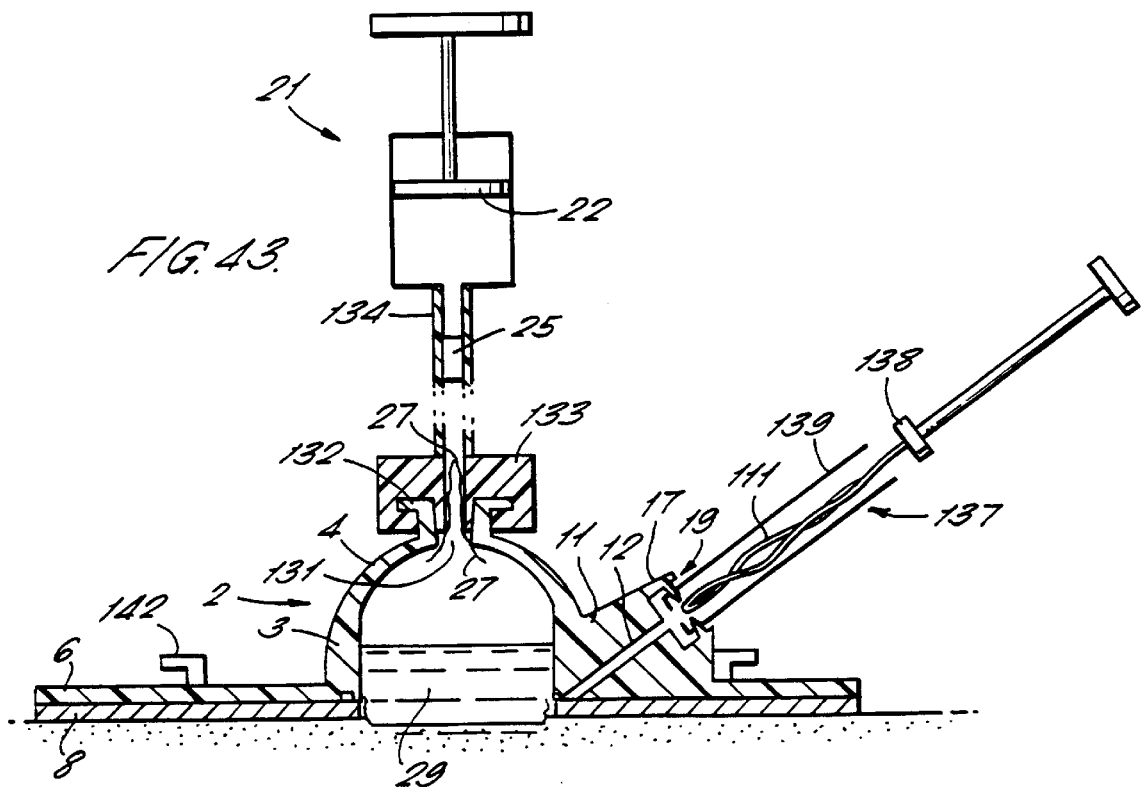
FIG. 43 is a schematic sectioned elevation of the apparatus of FIGS. 39 to 42 showing the disruption of a suction blister by means of the thread having been withdrawn from the chamber.

Ultimately the loop portion 112 is entirely withdrawn from the chamber 10 and at this time the position shown in FIG. 43 is reached in which the actuator piston 138 of the actuator 137 exits the actuator cylinder 139. Air is then admitted through the duct 12 via the open actuator cylinder 139 and the suction within the chamber 10 is rapidly equilibrated to atmospheric pressure. The resulting inflow of air via the access port 13 results in a corresponding outflow of air via the tube 134 in which the detached epidermis 27 of the disrupted suction blister 26 is entrained. In this way the detached epidermis may be disposed of automatically from the chamber 10.

The actuator 137 may then be removed from the apparatus 130 as shown in FIG. 44 by disconnecting the male and female connectors 19, 17 to release the actuator cylinder 139 from the ducted portion 11. The male luer connector 133 is similarly disconnected from the female luer connector 132 to expose the suction port 131 as shown in FIG. 44.

As shown in FIG. 45, the roof 4 of the cup 2 is then moved into a collapsed configuration in which it is retained by the insertion of a plug 140 which includes a stopper portion 141 extending into the female luer connector 132 in order to seal the suction port 131.

The plug 140 is secured in this position to the flange 6 by means of co-operating bayonet fittings 142. The plug 140 is dimensioned such that the collapsed roof does not touch the exposed dermis of the skin.

The duct 12 may be temporarily sealed by the insertion of a closure member 59 as shown in FIG. 45 into the female connector 17.

Figure 47:
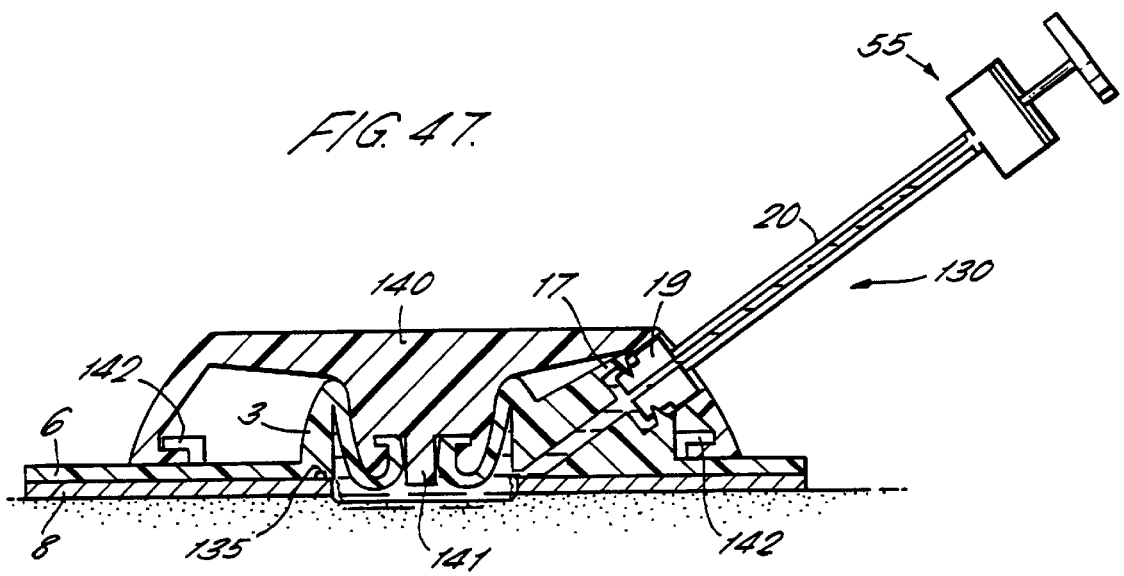
FIG. 47 is a schematic sectioned elevation of the apparatus of FIGS. 39 to 46 showing extraction of plasma filtrate by retraction of the syringe.

In order to commence the extraction of plasma filtrate from the chamber 10, a sampling device such as a syringe 55 shown in FIG. 46 may be coupled to the duct 12 be means of a male connector 19 and a tube 20. The extraction of plasma filtrate is illustrated in FIG. 47.

Figure 48:
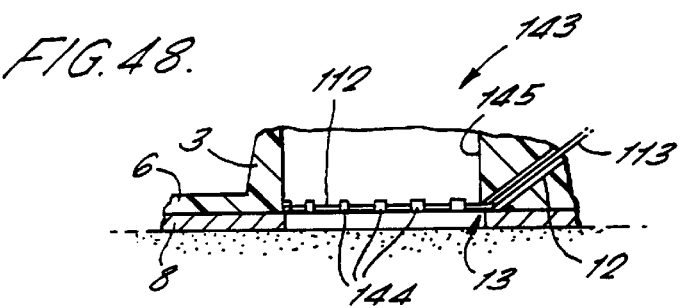
FIG. 48 is a schematic sectioned elevation of a further alternative apparatus in which a thread is retained peripherally within the chamber.
Figure 49:
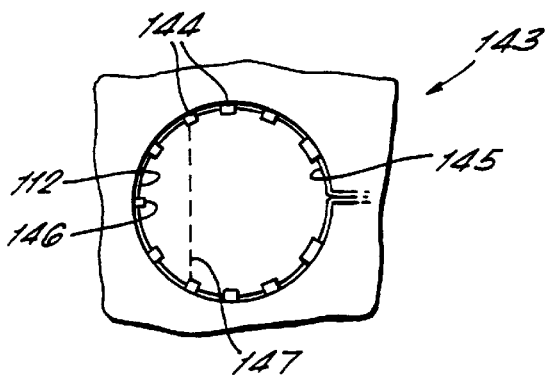
FIG. 49 is a plan view of the detail shown in FIG. 48.

The apparatus 130 of FIGS. 35 to 46 may alternatively be modified as shown in FIGS. 48 and 49 which show a further alternative apparatus 143 which will now be described using corresponding reference numerals to those of preceding Figures where appropriate for corresponding elements.

Instead of relying upon circular groove 135, apparatus 143 utilises a series of lugs 144 which project radially inwardly from the cylindrical inner surface 145 of the rim portion 3. The loop portion 112 is anchored against the inner surface 145 by the lugs 144 and thereby retained in an initial configuration which is approximately circular as shown in FIG. 49.

The size of the lugs 144 as measured in a circumferential direction varies according to the displacement of each lug relative to the access port 13. Specifically, the size of the lugs decreases with increasing displacement away from the access port 13 so that the loop portion 112 breaks away from the lugs in a controlled manner when placed under tension by pulling the end portions 113. The first separation of the loop portion from the lugs 144 will occur at the most distant lug 146 as shown in FIG. 49 and subsequently and progressively the loop portion will break away from lugs of increasing size as the end portions 113 continue to be pulled from the chamber via the access port 13.

This has the effect of continuing to maintain a linear portion (indicated for example by broken lines at 147 in FIG. 49) in a taut configuration so that the loop portion continues to provide cutting action as it passes through the suction blister. As shown in FIG. 49, the linear portion 147 will progressively and rapidly move from left to right as the loop portion 112 progressively breaks away from the lugs 144.

Figure 50:
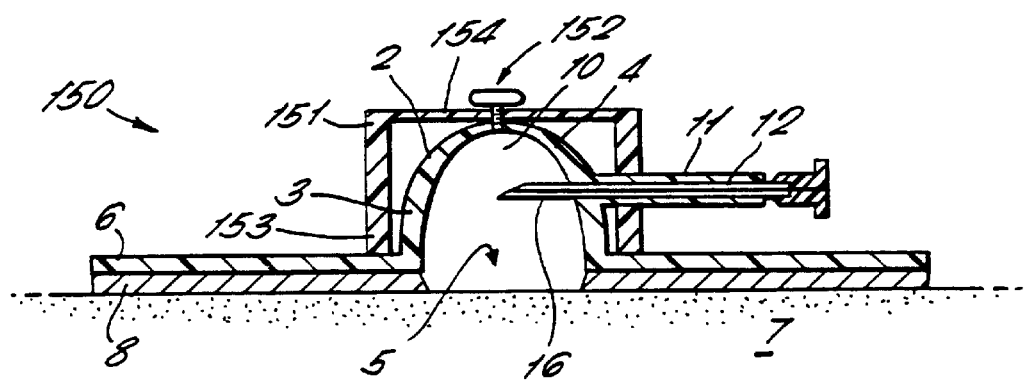
FIG. 50 is a schematic sectioned elevation of a further alternative apparatus.

A further alternative apparatus 150 is shown in FIG. 50 and will now be described using corresponding reference numerals to those of preceding Figures where appropriate for corresponding elements.

The apparatus 150 has a cup 2 of resiliently deformable plastics material having a shape memory such that in the absence of deformation it assumes the hemispherical shape shown in FIG. 50. The cup 2 has a rim portion 3 peripheral to a roof 4 which is normally held clear of an aperture 5 defined within the rim portion.

The rim portion merges at right angles with a flange 6 secured to a body 7 by means of an adhesive layer 8.

A ducted portion 11 defines a duct 12 through which a needle 16 extends in order to provide means for disrupting a suction blister formed within a chamber 10 defined by the cup 2.

The needle 16 may be withdrawn and suction applied within the chamber 10 by means of a suitable syringe as described above with reference to FIG. 1.

The apparatus 150 further includes a supporting structure 151 which fits over the cup 2 and which is releasably connected to the roof 4 by means of a fastener 152.

The supporting structure 151 consists of a stand off portion 153 which extends into contact with the upper surface of the flange 6 and which maintains a support 154 at a predetermined displacement above the flange, the fastener 152 thereby ensuring that the roof 4 is held at a fixed height relative to the flange.

The fastener 152 is shown in FIG. 50 as being a screw coupling. Other suitable forms of fastener may be utilised such as bayonet fittings, snap fitting fasteners or the like.

The supporting structure 151 is utilised to maintain the cup 2 in its fully expanded configuration during the formation of a suction blister by the application of suction within the chamber 10. Following the removal of suction and the disruption of a suction blister within the chamber 10, it will typically then be required to invert the roof 4 into its collapsed configuration in order to reduce the volume of the chamber 10 to assist in the efficient extraction of plasma filtrate as described above for example with reference to FIGS. 1 to 7.

By releasing the fastener 152, the supporting structure 151 may then be removed allowing access to manually apply deforming pressure to the roof. After being deformed into the collapsed configuration, the roof 4 may be maintained in the collapsed configuration of minimum chamber volume by any suitable means such as a plug 33 described above with reference to FIG. 7.

The embodiments of the present invention described above with reference to FIGS. 1 to 7, 11 to 24 and 30 to 38 may all be adapted to utilise a supporting structure 151 of the type described with reference to FIG. 50.

Alternative embodiments of the present invention are envisaged in which for example the flange of any of the above embodiments incorporates means for heating the flange in order to effect warming of the skin surrounding the aperture. Such warming has the effect of enhancing the rate at which plasma filtrate is produced both during the blister forming period and subsequently during the production of plasma filtrate for sampling.

Apparatus in accordance with the present invention may alternatively be modified to include electrodes and associated circuitry to apply the technique of iontophoresis between the skin at the erosion and fluid in contact with the skin. A first electrode may for example be positioned peripherally of the erosion and located in the flange of the apparatus, a second electrode being located so as to project into fluid in contact with the exposed dermis. The passage of a low level electrical current between the electrodes may then be utilised to enhance the rate of passage of electrically charged molecules such as peptides and proteins either into or out of the dermis.

The absence of the epidermis at the skin erosion has the effect of significantly reducing the electrical resistance of the skin thereby requiring the level of current for iontophoresis to be significantly reduced. A small solar cell may therefore be utilised as a power supply.

The flange is preferably secured to the skin using an inner annular region of acrylic adhesive and an outer annular region of hydrocoloid adhesive.

The cup is typically manufactured of a transparent plastics material selected to provide sufficient rigidity to prevent the roof collapsing when the air pressure within the chamber is reduced by the application of suction, the roof being required to remain in its expanded configuration when a negative pressure of 400 millimetres of mercury is applied.

The cup may be removably connected to the flange in order to provide access for cleaning the skin erosion.

Typically the aperture defined by the cup will be in the range of 2 to 10 milimetres and preferably the access port 13 is located at least one millimetre clear of the adhesive coating of the flange.

The cup may be provided with separate inlet and outlet ducts to enable a continuous flow of a carrier fluid to be passed through the chamber, preferably maintaining the flow by suction at the outlet such that a negative pressure is maintained within the chamber.

The outlet tube may be connected to a pad of absorbent material to dispose of excess plasma filtrate.

The rim portion may be recessed into an annular furrow in order to discourage direct contact with the epidermis of the suction blister during its formation.

The internal walls of the roof may be provided with means for enhancing friction between the roof and the epidermis of the suction blister, the friction means being either in the form of surface roughness or gripping formations such as ribs.

Apparatus in accordance with the present invention has been demonstrated to be able to produce volumes of plasma filtrate in the range 50 to 200 micro litres in a period of 30 minutes without causing discomfort. Sampling using the application of the apparatus may be repeatedly carried out at the same skin site over an extended period of up to 9 to 12 days. During such an extended period the healing process tends to decrease the available area of the erosion. For example, a six milimetre erosion would decrease to approximately two milimetres diameter after a period of about six to nine days. This decrease in size does not have an appreciable effect on the rate of production of plasma filtrate, this rate of production tending to be abruptly curtailed when the epithelial barrier has reformed.

Such a reformed epithelial barrier can be removed by the application of an adhesive patch which is then stripped repeatedly (for approximately ten times consecutively) leaving the erosion available for further sampling. This stripping procedure is however feasible only if the barrier layer has reformed within the past 12 hours.

The interior walls of the cup may be treated with antibacterial agents. The interior walls, including the walls of tubes contacting fluid samples, may also be heparinized to prevent formation of clots.

Figure 51:
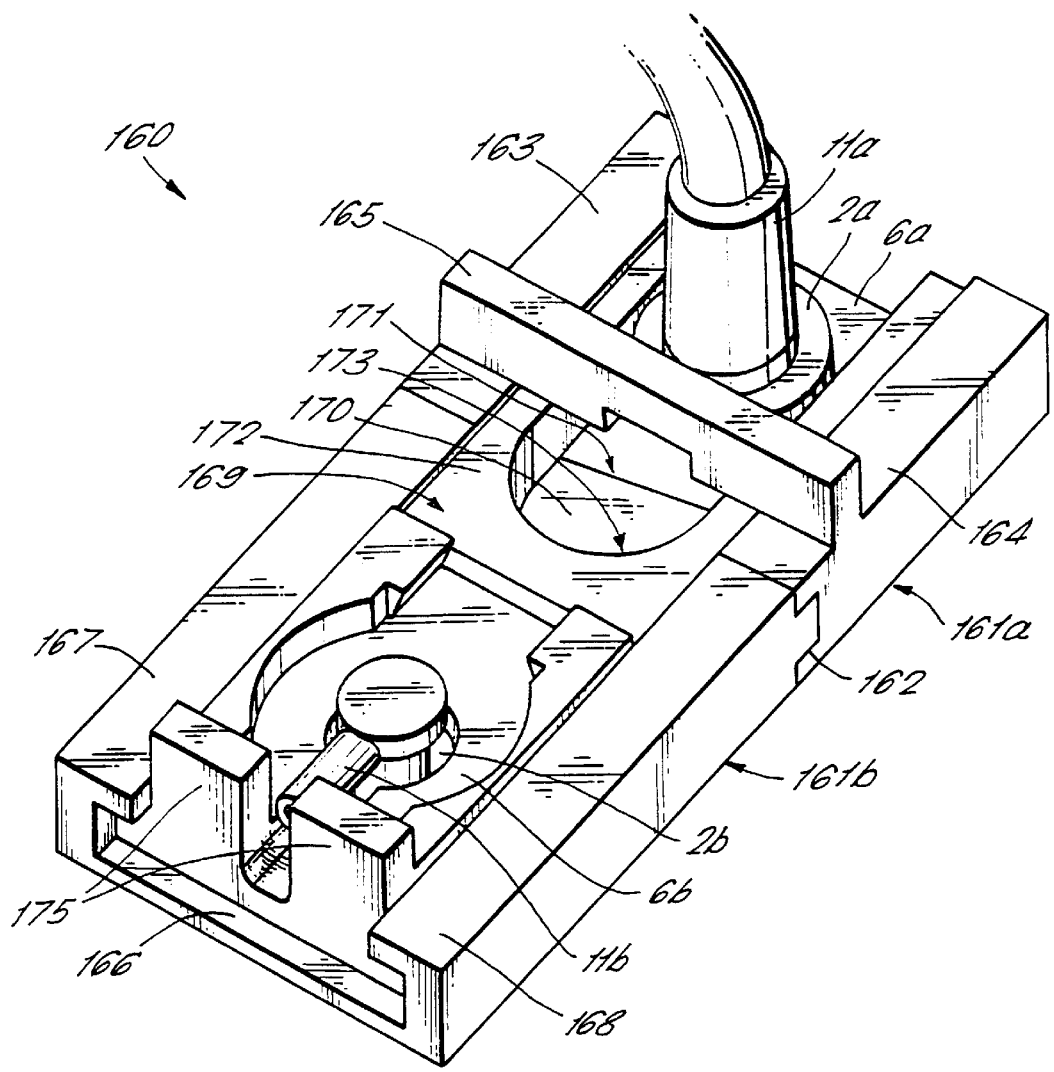
FIGS. 51 to 53 show schematic perspective views of another alternative apparatus.
Figure 52:
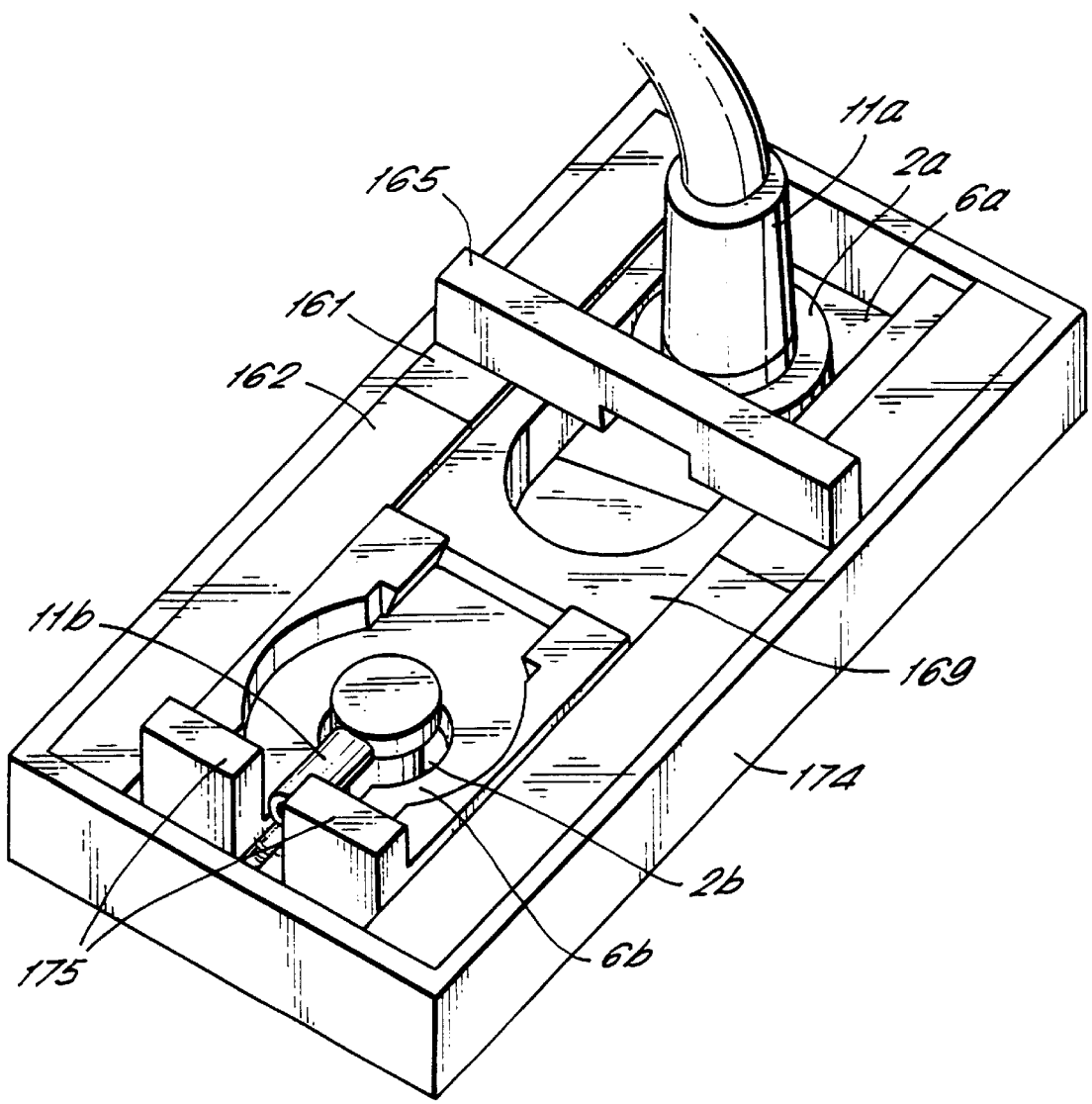
Figure 53:
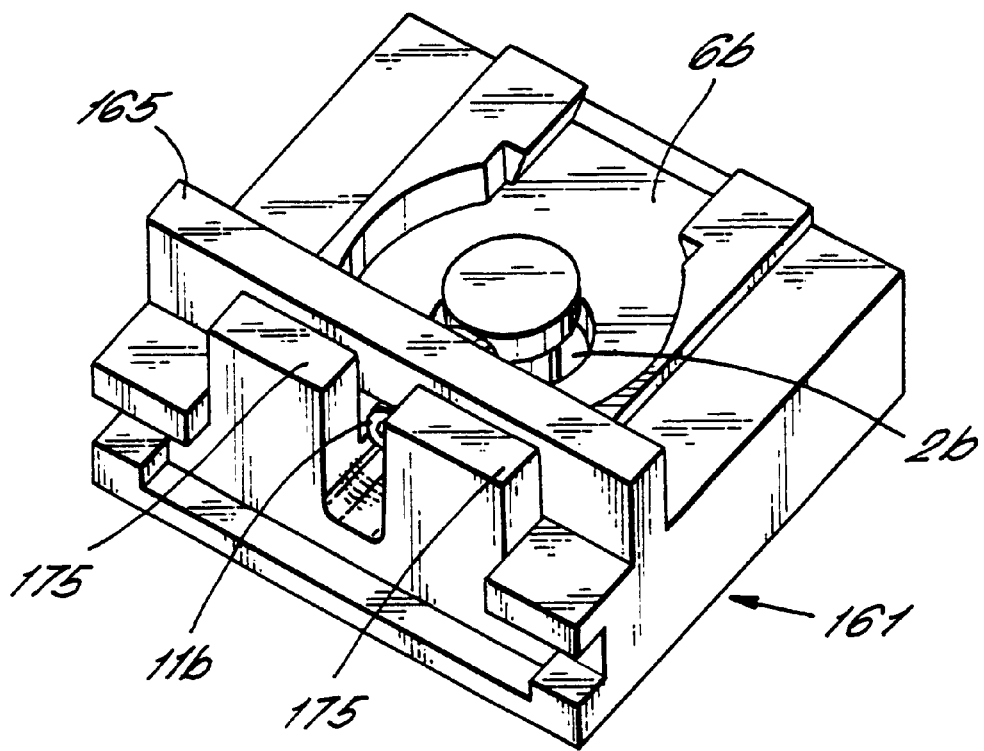

Another alternative apparatus 160 is shown in FIGS. 51 to 53 and will now be described using corresponding reference numbers to those with preceding figures where appropriate for corresponding elements.

The apparatus 160 comprises two cups 2a, 2b. The first cup 2a shown on the right hand side in FIG. 51 is, as described further below, used only for forming a suction blister and therefore can be made of rigid plastics material. The second cup 2b shown on the left hand side of FIG. 51 is used as a sampling cup for collecting plasma filtrate and is therefore made of resiliently deformable plastics material having a shape memory such that in the absence of deformation it assumes a hemispherical shape. Thus, the second cup 2b is similar to the cups described previously in relation to other embodiments.

Both cups 2a,2b comprise a roof with a peripheral rim portion defining an aperture. The rim portion of each cup merges at right angles with a respective flange 6a, 6b. Both flanges 6a,6b are extended out into substantially rectangular shapes having straight edges.

The blister forming cup 2a includes a ducted portion 11a defining a duct in communication with the chamber defined within the cup for connection to a suction device (not shown). Preferably, the tubing connecting the ducted portion 11a to the suction device will include a slug of liquid as an indicator as described previously (for example slug 25 in FIGS. 1 and 2). Similarly, the sampling cup 2b has a ducted portion 1ib defining a duct communicating with the chamber defined within the cup.

The flange 6a which is integral with the blister forming cup 2a is formed with L-section members along opposite edges which act as guide rails 163,164. Thus, the flange 6a with its guide rails 163,164 forms a first track unit 161a which is described further below. The thickness of the flange 6a decreases towards the rim portion of the cup 2a.

This first track unit 161a is releasably attached to a second track unit 161b by means of mating formations 162 such as corresponding protrusions and recesses as seen in FIG. 51.

The second track unit 161b comprises a flat plate 166 also formed with L-section flanges on opposite edges to create opposed guide rails 167,168 co-linear with the guide rails 163,164 of the first track unit 161a.

The sampling cup 2b, with its integral flange 6b, is mounted on the second track unit 161b with opposite edges of the flange 6b slidably received in the guide rails 167,168.

Situated between the two cups 2a,2b is a tome or cutting device 169. The cutting device 169 comprises a planar cutting blade 170 with a cutting edge 171 facing the blister forming cup 2a. The cutting edge 171 of the blade 170 may be perpendicular to the direction of the guide rails 163,164, 167,168 but it is preferably positioned to be slightly oblique, for example at an angle of approximately 10° to 15° to the perpendicular. The blade 170 is held in a U-shaped substantially supporting mount 172 having a semicircular cut-out 173 at the base of the U adjacent the blade 170. The limbs of the U-shaped mount 172 extend forwardly of the cutting blade 170 and either side the blister forming cup 2a. The extended limbs are a safety feature which helps to prevent accidental access to the cutting blade 170 by a user. Opposed edges of the mount 172 are slidably received in the guide rails 163,164,167,168 provided by the first and second parts 161a,161b of the track unit.

The flange 6b of sampling cup 2b may have formations which mate with corresponding formations on the mount 172 of the cutting device 169 in order to releasably attach the two components together. However, the apparatus 160 is configured such that the separation line between the flange 6b and the mount 172 is not co-linear with the separation line between the first and second track units 161a,161b. This feature gives greater stability and rigidity to the assembled apparatus 160.

In the initial stages of operation of the apparatus 160, an outer rectangular frame 174 is positioned surrounding the first and second track units 161a,161b as seen in FIG. 52. This frame 174 holds all the components together and prevents movement of the sampling cup 2b and the cutting device 169 along the guide rails 163,164,167,168.

The underside of the flange 6a of the blister forming cup 2a is coated with an adhesive to enable it to be adhered to the skin with an airtight seal. As mentioned in relation to previous embodiments, the adhesive preferably consists of an annular band of acrylic adhesive adjacent to the rim portion of the blister forming cup 2a and an outer annular band of hydrocolloid adhesive.

In operation, the apparatus 160 is configured as shown in FIG. 52 with the outer frame 174 surrounding all the components. The part 161a being coated with an adhesive are applied to an area of skin. Suction is applied to the blister forming cup 2a as described previously in order to cause a blister to form within the cup 2a. Typically, a suction of 200 mmHg is applied to create the blister. When a blister has formed as required, for example as shown by the movement of an indicator slug of liquid in the tube, suction is removed in order to equalise the pressure in the blister forming cup 2a. This allows the intact skin at the site of the erosion to fall back to the same level as the surrounding skin rather than bulging upwardly, for example as shown in FIG. 2.

Once the pressure has been equalized, the outer frame 174 is removed which allows movement of the other components along the guide rails 163,164,167,168. The sampling cup 2b is pushed towards the blister forming cup 2a, i.e towards the right hand side as seen in FIG. 51. This action in turn pushes the cutting device 169 towards the blister forming cup 2a. The cutting blade 170 travels across the upper surface of the flange 6a thereby severing the blister forming cup 2a from the flange 6a as well as severing the blister from the skin. Thus, the blister forming cup 2a is received in the semicircular cut out 173 formed in the mount 172 of the cutting device 169.

Preferably, the frame 174 and the ducted portion 11a should be associated with one another to ensure that the frame 174 cannot be removed while suction is still being applied to the cup 2a. For example, the ducted portion 11a could be secured to the frame 174 to prevent removal of the frame 174 unless the ducted portion 11a is severed or ruptured. Such a feature would ensure that the cutting device 169 cannot be moved until pressure in the cup 2*a* is equalised and the skin at the erosion site no longer bulges upwardly into the path of the blade 170.

If the sampling cup 2*b* is then pushed even further along the guide rails towards the right, the cutting device 169 and the severed blister forming cup 2*a* are forced off the end of the guide rails 163,164 and out of the apparatus 160. The flange 6*b* slides over the upper surface of flanges 6*a* and the sampling cup 2*b* is thus moved into position over the site of the erosion. As shown in FIGS. 51 to 53, the flange 6*b* of the sampling cup 2*b* may be formed with one or more upstanding pillars 175 which engage against the crossbar 165 which acts as a stop member to locate the sampling cup 2*b* exactly over the site of the erosion. Furthermore, the dimensions of the guide rails 163,164 formed by the first track unit 161*a* are configured such that, as the sampling cup 2*b* is moved into position over the erosion, the guide rails 163,164 progressively press the edges of the flange 6*b* downwardly to ensure an airtight seal between the flange 6*b* and the flange 6*a*.

When the sampling cup 2*b* is in this position the second track unit 161*b* becomes superfluous and can be detached from the first unit 161*a* and removed, leaving only sampling cup 2*b* and the first track unit 161*a* as shown in FIG. 53. The ducted part 11*b* of the sampling cup 2*b* can now be connected to a suction device in order to draw plasma filtrate from the erosion site into the cup 2*b*. Once the cup 2*b* becomes filled with plasma filtrate, suction is removed to equalise pressure in the cup 2*b* and the plasma filtrate can be evacuated from the cup by light compression by a fingertip to deform the roof of the cup 2*b* and expel plasma filtrate through the ducted portion 11*b*.

Typically, the suction used to draw plasma filtrate is in the range of −50 to −200 mmHg. At −200 mmHg a typical rate of plasma filtrate formation is 2 to 3 $\mu$l per minute.

After plasma filtrate has been expelled from the cup 2*b* by compression, the cup can be retained in the collapsed position by means of a plugging device as described previously e.g in relation to FIG. 7. Equally, during suction the cup can be maintained in the expanded state for example by an external stabilising means as shown in FIG. 50.

Apparatus of the type shown in FIGS. 51 to 53 can be made easily from moulded plastics material and provides a device which is relatively simple to manipulate while keeping the size of the blister created to a minimum.

What is claimed is:

1. Apparatus for use in a suction blister technique of sampling fluid from the human or animal body, the apparatus comprising first and second cups, each cup defining a chamber and having a roof and a rim portion defining an aperture communicating with the chamber and a flange extending outwardly from the rim portion, a cutting device comprising cutting means mounted in a support member; and guide means associated with the flange of the first cup and slidably receiving the cutting device and the second cup; wherein the cutting device and the second cup are movable along the guide member such that the cutting means severs the first cup from its respective flange and the second cup assumes the position of the first cup.

2. Apparatus as claimed in claim 1, wherein the guide means comprises a pair of guide rails formed along opposite edges of the flange of the first cup.

3. Apparatus as claimed in claim 2, wherein the guide means further comprises a second pair of guide rails releasably attached to the first pair.

4. Apparatus as claimed in claim 3, wherein the first pair of guide rails comprises a pair of opposed L-section members formed on opposing edges of the flange of the first cup.

5. Apparatus as claimed in claim 3 or claim 4, wherein the second pair of guide rails comprises a plate having a pair of opposed L-section members along opposite edges.

6. Apparatus as claimed in claim 1, wherein the second cup and the cutting device are movable linearly along the guide means.

7. Apparatus as claimed in claim 1, wherein the cutting device is positioned between the first and second cups.

8. Apparatus as claimed in claim 1, wherein the cutting means comprises a cutting blade having a cutting edge angled at approximately 75° to 80° to the direction of movement of the cutting device along the guide means.

9. Apparatus as claimed in claim 1, further comprising removable retaining means for preventing movement of the second cup and the cutting device along the guide means.

10. Apparatus as claimed in claim 9, wherein the retaining means comprises a frame means surrounding the guide means.

11. Apparatus as claimed in claim 1, wherein means is provided to locate the second cup as it is moved into the position of the first cup.

12. Apparatus as claimed in claim 11, wherein the locating means comprises co-operating abutment members on the guide means and the second cup.

13. Apparatus of claim 1, wherein the outwardly extending flange on at least one of said first and second cups is annular flange.

14. A method of forming a suction blister and sampling fluid formed at the site of the blister, the method comprising the following steps:
   (a) adhesively sealingly securing to an area of skin at least a first cup that defines a first chamber and that includes a first roof with a first rim portion defining a first aperture communicating with said first chamber, and includes a first flange extending outwardly from said first rim portion such that a selected portion of said skin is accessible to said first chamber;
   (b) providing a second cup that defines a second chamber and that includes a second roof with a second rim portion defining a second aperture communicating with said second chamber, and includes a second flange extending outwardly from said second portion;
   (c) disposing a cutting device in a support member that is guideably movable in alignment with said first flange;
   (d) applying suction to said first chamber for a period of time sufficient to form a blister at a blister site within said first chamber;
   (e) equilibrating pressure within said first chamber to atmospheric pressure;
   (f) moving said cutting device to sever said first cup from said first flange and to sever said blister from said skin; and
   (g) causing said second cup to assume a position over said skin previously taken by said first cup such that said blister site is accessible to said second chamber.

15. The method of claim 14, further including the following steps:
   (h) applying suction to said second chamber to draw fluid from said blister site;
   (i) equilibrating pressure within said second chamber to atmospheric pressure; and
   (j) deforming said second chamber to expel fluid therefrom.

16. The method of claim 14, wherein at least one of said first flange and second flange is an annular flange.

* * * * *